(12) United States Patent
Perni et al.

(10) Patent No.: US 12,012,381 B2
(45) Date of Patent: Jun. 18, 2024

(54) DIMETHYLTRYPTAMINE ANALOGUES AS NITRIC OXIDE DELIVERY DRUGS

(71) Applicant: ATAI Therapeutics, Inc., New York, NY (US)

(72) Inventors: Robert B. Perni, Marlborough, MA (US); Glenn Short, Scituate, MA (US); Tanweer A. Khan, Bridgewater, NJ (US)

(73) Assignee: ATAI THERAPEUTICS, INC., Encinitas, CA (US)

( * ) Notice: Subject to any disclaimer, the term of this patent is extended or adjusted under 35 U.S.C. 154(b) by 0 days.

(21) Appl. No.: 18/147,499

(22) Filed: Dec. 28, 2022

(65) Prior Publication Data

US 2023/0227407 A1     Jul. 20, 2023

Related U.S. Application Data

(60) Provisional application No. 63/295,199, filed on Dec. 30, 2021.

(51) Int. Cl.
C07D 209/16 (2006.01)

(52) U.S. Cl.
CPC ........ C07D 209/16 (2013.01); *C07B 2200/05* (2013.01)

(58) Field of Classification Search
CPC .................................................. C07D 209/16
See application file for complete search history.

(56) References Cited

U.S. PATENT DOCUMENTS

| | | | |
|---|---|---|---|
| 5,340,838 | A | 8/1994 | Gidda et al. |
| 5,705,527 | A * | 1/1998 | Ishihara ............. C07C 237/22 |
| | | | 548/496 |
| 6,201,025 | B1 | 3/2001 | Dax et al. |
| 6,436,950 | B1 | 8/2002 | Achari et al. |
| 8,268,856 | B2 | 9/2012 | Hamann et al. |
| 9,388,395 | B2 | 7/2016 | Nazor et al. |
| 9,720,005 | B2 | 8/2017 | McConnell et al. |
| 11,242,318 | B2 | 2/2022 | Nivorozhkin et al. |
| 11,332,441 | B2 | 5/2022 | Chadeayne |
| 11,602,521 | B2 | 3/2023 | Rao et al. |
| 11,643,391 | B2 * | 5/2023 | Perni ............... C07D 209/14 |
| | | | 514/80 |
| 2002/0115715 | A1 | 8/2002 | Dax et al. |
| 2003/0079301 | A1 | 5/2003 | Sauter et al. |
| 2004/0235899 | A1 | 11/2004 | Maria Assunta et al. |
| 2005/0152858 | A1 | 7/2005 | Bertz et al. |
| 2005/0245594 | A1 | 11/2005 | Sutter et al. |
| 2005/0250839 | A1 * | 11/2005 | Marnett ............. C07C 235/34 |
| | | | 514/420 |
| 2007/0099909 | A1 | 5/2007 | Chen et al. |
| 2008/0248511 | A1 | 10/2008 | Daily et al. |
| 2008/0318957 | A1 | 12/2008 | Glinka et al. |
| 2010/0113539 | A1 | 5/2010 | Scott et al. |
| 2012/0028995 | A1 | 2/2012 | Ansorge et al. |
| 2015/0071994 | A1 | 3/2015 | Schentag et al. |
| 2015/0346226 | A1 | 12/2015 | McConnell et al. |
| 2016/0002195 | A1 * | 1/2016 | Makriyannis ........... A61P 29/00 |
| | | | 548/362.5 |
| 2019/0315689 | A1 | 10/2019 | Chen et al. |
| 2020/0325124 | A1 | 10/2020 | Lavoie et al. |
| 2020/0390746 | A1 | 12/2020 | Rands et al. |
| 2020/0397752 | A1 | 12/2020 | Perez Castillo et al. |
| 2021/0145851 | A1 | 5/2021 | Stamets |
| 2021/0236523 | A1 | 8/2021 | Schindler et al. |

(Continued)

FOREIGN PATENT DOCUMENTS

EP            1336602 A1 *  8/2003  ........... C07C 291/02
WO      WO-9323364 A1     11/1993

(Continued)

OTHER PUBLICATIONS

Bugaenko; Russ. Chem. Rev. 2019, 88, 99-159. https://doi.org/10.1070/RCR4844 (Year: 2019).*
Chegaev; Journal of Pineal Research 2007, 42, 371-385. https://doi.org/10.1111/j.1600-079x.2007.00429.x (Year: 2007).*
Gribble; J. Chem. Soc., Perkin Trans. 1, 2000, 1045-1075. https://doi.org/10.1039/A909834H (Year: 2000).*
Humphrey; Chem. Rev. 2006, 106, 7, 2875-2911. https://doi.org/10.1021/cr0505270 (Year: 2006).*

(Continued)

*Primary Examiner* — Daniel R Carcanague

(74) *Attorney, Agent, or Firm* — COOLEY LLP

(57) ABSTRACT

Provided herein are compounds of Formula (I), (II), or a pharmaceutically acceptable salt thereof. Also provided herein are pharmaceutical compositions comprising a compound of Formula (I), (II), or pharmaceutically acceptable salt thereof, and methods of using a compound of Formula (I), (II), or a pharmaceutically acceptable salt thereof.

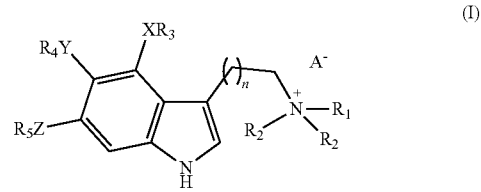

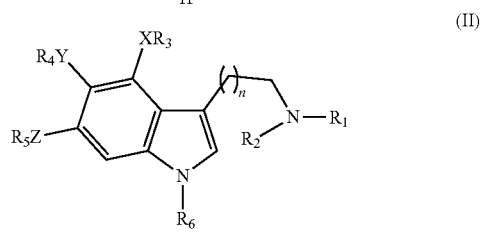

33 Claims, No Drawings

(56) References Cited

U.S. PATENT DOCUMENTS

| | | |
|---|---|---|
| 2021/0277433 A1 | 9/2021 | Protzko |
| 2021/0346347 A1 | 11/2021 | Witowski et al. |
| 2021/0363104 A1 | 11/2021 | Nivorozhkin et al. |
| 2021/0378969 A1 | 12/2021 | Rands et al. |
| 2021/0395201 A1 | 12/2021 | Rands et al. |
| 2022/0031662 A1 | 2/2022 | Terwey |
| 2022/0071958 A1 | 3/2022 | Terwey |
| 2022/0079881 A1 | 3/2022 | Modi |
| 2022/0267267 A1 | 8/2022 | Feilding-Mellen |
| 2022/0304980 A1 | 9/2022 | Arnold et al. |
| 2022/0339139 A1 | 10/2022 | Rao et al. |
| 2022/0388956 A1 | 12/2022 | Short et al. |
| 2023/0041584 A1* | 2/2023 | Perni .............. C07D 209/14 |
| 2023/0066720 A1 | 3/2023 | Perni et al. |
| 2023/0099972 A1 | 3/2023 | Rao et al. |
| 2023/0227421 A1* | 7/2023 | Perni .............. C07D 307/79 |
| | | 514/452 |

FOREIGN PATENT DOCUMENTS

| | | | |
|---|---|---|---|
| WO | WO-0041755 A1 | 7/2000 | |
| WO | WO-0051672 A1 | 9/2000 | |
| WO | WO-0211800 A2 | 2/2002 | |
| WO | WO-02068029 A2 | 9/2002 | |
| WO | WO-02068030 A2 | 9/2002 | |
| WO | WO-02068031 A2 | 9/2002 | |
| WO | WO-02068032 A2 | 9/2002 | |
| WO | WO-03000310 A2 | 1/2003 | |
| WO | WO-03020350 A1 | 3/2003 | |
| WO | WO-03026559 A2 | 4/2003 | |
| WO | WO-03082393 A1 | 10/2003 | |
| WO | WO-03084591 A1 | 10/2003 | |
| WO | WO-03090812 A2 | 11/2003 | |
| WO | WO-2006099416 A1 * | 9/2006 | ........... C07D 209/12 |
| WO | WO-2010151258 A1 | 12/2010 | |
| WO | WO-2011041870 A1 * | 4/2011 | ........... A61K 31/223 |
| WO | WO-2013063492 A1 | 5/2013 | |
| WO | WO-2019213551 A1 | 11/2019 | |
| WO | WO-2020037372 A1 | 2/2020 | |
| WO | WO-2020176597 A1 | 9/2020 | |
| WO | WO-2020181194 A1 * | 9/2020 | ............. A61K 31/13 |
| WO | WO-2021226416 A1 | 11/2021 | |
| WO | WO-2021244831 A1 | 12/2021 | |
| WO | WO-2021250434 A1 | 12/2021 | |
| WO | WO-2021250435 A1 | 12/2021 | |
| WO | WO-2022061242 A1 | 3/2022 | |
| WO | WO-2022082058 A1 | 4/2022 | |
| WO | WO-2022232179 A1 | 11/2022 | |
| WO | WO-2022235514 A1 | 11/2022 | |
| WO | WO-2022235529 A1 | 11/2022 | |
| WO | WO-2022246572 A1 | 12/2022 | |
| WO | WO-2022251351 A1 | 12/2022 | |
| WO | WO-2022261383 A1 | 12/2022 | |
| WO | WO-2023036473 A1 | 3/2023 | |
| WO | WO-2023055992 A1 | 4/2023 | |

OTHER PUBLICATIONS

Huttunen; Pharmacol Rev 2011, 63, 750-771. https://doi.org/10.1124/pr.110.003459 (Year: 2011).*

Kline; Journal of Medicinal Chemistry 1982, 25, 908-913. https://doi.org/10.1021/jm00350a005 (Year: 1982).*

Wey; Journal of Medicinal Chemistry 2007, 50, 6367-6382. https://doi.org/10.1021/jm0611861 (Year: 2007).*

ACS Chem. Neuroscience, 2018, pp. 1582-1590.

Safety Data Sheet, Caymanchem.com, Cayman Chemical, Apr. 21, 2021, 6 pages.

Andersson et al., "Psychoactive substances as a last resort—a qualitative study of self-treatment of migraine and cluster headaches," Harm Reduction Journal, Dec. 2017, 10 pages.

Archer et al., "5-Methoxy-N, N-dimethyltryptamine-induced analgesia is blocked by alpha-adrenoceptor antagonists in rats," British J. Pharmac., Oct. 1986, pp. 293-298.

Baker et al., "Neurochemical and neuropharmacological investigation of N-cyanoethyltryptamine, a potential prodrug of tryptamine," Proc West Pharmacol Soc., 1987, 307-11.

Barsuglia et al., "Intensity of mystical experiences occasioned by 5-MeO-DMT and comparison with a prior psilocybin study," Front. Psychol., Dec. 2018, 6 pages.

Benneyworth et al., "Complex discriminative stimulus properties of (+)lysergic acid diethylamide (LSD) in C57BI/6J mice," Psychopharmacology (2005) 179, 854-862.

Brito-Da-Costa, et al., Toxicokinetics and toxicodynamics of ayahuasca alkaloids N, N-dimethyltryptamine (DMT), harmine, harmaline and tetrahydroharmine: clinical and forensic impact., Pharmaceuticals, Oct. 2020, 36 pages.

Cameron et al. "A non-hallucinogenic psychedelic analogue with therapeutic potential", Nature, 2021, pp. 474-479.

Carhart-Harris et al., "Psilocybin for treatment-resistant depression: fMRI-measured brain mechanisms," Scientific Reports, Oct. 2017, 11 pages.

Carter et al., "Modulating the rate and rhythmicity of perceptual rivalry alternations with the mixed 5-HT2A and 5-HT1A agonist psilocybin," Neuropsychopharmacology, Jun. 2005, pp. 1154-1162.

CAS Registry No. 1152718-19-8, Benzenemethanamine, N-[4-(1,1-dimethylethyl)cyclohexyl]-2,4-difluoro-a-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1,1-dimethylpropyl)-, trans-(9CI), Jun. 1, 1990, 1 page.

CAS Registry No. 127456-44-4, 1H-Inden-5-ol, 6-[[[4-(1,1-dimethylethyl)cyclohexyl]amino]methyl]-2,3-dihydro-, trans-(9CI), Jun. 1, 1990, 1 page.

CAS Registry No. 127456-45-5, Phenol, 4-(1, 1-dimethylethyl)-2-[[[4-(1,1-dimethylethyl)cyclohexyl]amino]methyl]-, trans-(9CI), Jun. 1, 1990, 1 page.

CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans-(9CI), Jun. 1, 1990, 1 page.

CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.

CAS Registry No. 127456-56-8, Phenol, 4-chloro-2-[[[4-(1,1-dimethylethyl)cyclohexyl]amino]methyl]-, trans-(9CI), Jun. 1, 1990, 1 page.

CAS Registry No. 127456-57-9, Phenol, 2-[[[4-(1,1-dimethylethyl)cyclohexyl]amino]methyl]-4-fluoro-, trans-(9CI), Jun. 1, 1990, 1 page.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1,1-dimethylpropyl)cyclohexyl]-2,3-difluoro-, Dec. 5, 2012, 1 page.

CAS Registry No. 1456349-79-3, Benzenemethanamine, 2,3-dichloro-N-[4-(1,1-dimethylpropyl)cyclohexyl]-, Oct. 6, 2013, 1 page.

CAS Registry No. 1458497-71-6, Benzenemethanamine, 2,4-dichloro-N-[4-(1,1-dimethylethyl)cyclohexyl]-a-methyl-, Oct. 15, 2013, 1 page.

CAS Registry No. 1459328-13-2, Phenol, 2-bromo-4-[[[4-(1,1-dimethylpropyl)cyclohexyl]amino]methyl]-, Oct. 16, 2013, 1 page.

CAS Registry No. 1490220-45-5, Benzenemethanamine, 2-bromo-5-chloro-N-[4-(1,1-dimethylpropyl)cyclohexyl]-, Dec. 8, 2013, 1 page.

CAS Registry No. 1515984-46-9, Benzamide, N-(4-aminocyclohexyl)-3-chloro-N,5-dimethyl-, Jan. 10, 2014, 1 page.

CAS Registry No. 1542027-51-9, Phenol, 3-chloro-2-[[[4-(1,1-dimethylpropyl)cyclohexyl]amino]methyl]-, Feb. 11, 2014, 1 page.

(56) References Cited

OTHER PUBLICATIONS

CAS Registry No. 1624268-56-9, Benzamide, 4-[[[4-(1,1-dimethylethyl)cyclohexyl]amino]methyl]-N-methyl-, Sep. 22, 2014, 1 page.
CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1-dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[(3-chloro-5-methylphenyl)methyl]amino]-, Nov. 15, 2016, 1 page.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1, 1-dimethylethyl)-2-[[[trans-4-(1,1-dimethylethyl)cyclohexyl]amino]methyl]-6-methyl-, Dec. 6, 2004, 1 page.
Chegaev, et al., NO-donor melatonin derivatives: synthesis and in vitro pharmacological characterization, Journal of pineal research, May 2007, pp. 371-385.
Chen, et al., Structure-activity relationships in a series of 5-[(2, 5-dihydroxybenzyl) amino] salicylate inhibitors of EGF-receptor-associated tyrosine kinase: importance of additional hydrophobic aromatic interactions, Journal of Medicinal Chemistry, Mar. 1994, pp. 845-859.
ClinicalTrials.gov, Effects of Dimethyltryptamine in Healthy Subjects (DMT), Apr. 20, 2020, 9 pages, entire document, especially p. 2 table, p. 4 table row 1.Retrieved on Jun. 24, 2022 from https://clinicaltrials.gov/ct2/show/NCT0435304.
Cocchi et al., Novel Psychoactive Phenethylamines: Impact on Genetic Material, International Journal of Molecular Sciences, 2020, 17 pages.
Corne, A Possible Correlation between Drug-Induced Hallucinations in Man and a Behavioural Response in Mice, Psychopharmacolgia (Berl.), 1967, pp. 65-78.
Custodio et al., 25B-NBOMe, a novel N-2-methoxybenzyl-phenethylamine (NBOMe) derivative, may induce rewarding and reinforcing effects via a dopaminergic mechanism: evidence of abuse potential, Addiction Biology, Nov. 2019, 12 pages.
Dakic et al., Short term changes in the proteome of human cerebral organoids induced by 5-MeO-DMT, Scientific Reports, 2017, 13 pages.
Dalgleish, et al., Transdiagnostic approaches to mental health problems: Current status and future directions, J. Consult Clin Psychology, Mar. 2020, pp. 179-195.
Davis et al., 5-methoxy-N, N-dimethyltryptamine (5-MeO-DMT) used in a naturalistic group setting is associated with unintended improvements in depression and anxiety, The American Journal of Drug and Alcohol Abuse, 2019, 10 pages.
De Barros et al., "Synthesis of 25X-BOMes and 25X-NBOHs (X = H, I, Br) for pharmacological studies and as reference standards for forensic purposes," Tetrahedron Letters, Mar. 2021, 4 pages.
Dunlap et al., Identification of psychoplastogenic N, N-dimethylaminoisotryptamine (isoDMT) analogues through structure-activity relationship studies, J. Med. Chem. 2020, pp. 1142-1155.
Durham, Regulation of calcitonin gene-related peptide secretion by a serotonergic antimigraine drug, The Journal of Neuroscience, May 1, 1999, pp. 3423-3429.
Glennon et al., Influence of amine substituents on 5-HT2A versus 5-HT2C binding of phenylalkyl-and indolylalkylamines, Journal of Medicinal Chemistry, 1994, pp. 1929-1935.
Gonzalez-Maeso et al., "Hallucinogens Recruit Specific Cortical 5-HT2A Receptor-Mediated Signaling Pathways to Affect Behavior," Neuron, Feb. 2007, 439-452.
Halberstadt et al., Differential contributions of serotonin receptors to the behavioral effects of indoleamine hallucinogens in mice, J Psychopharmacol., Nov. 2011, pp. 1548-1561.
Halberstadt, Recent Advances in the Neuropsychopharmacology of Serotonergic Hallucinogens, Behav. Brain Res., 2015, pp. 99-120.
Hamada et al., Water-soluble prodrugs of dipeptide HIV protease inhibitors based on O-→N intramolecular acyl migration: Design, synthesis and kinetic study, Bioorg Med Chem., Jan. 2004, pp. 159-170.
Hansen et al., Synthesis and pharmacological evaluation of N-benzyl substituted 4-bromo-2,5-dimethoxyphenethylamines as 5-HT2A/2C partial agonists, Bioorganic & Medicinal Chemistry, 2015, pp. 3933-3937.
Hansen et al., Synthesis and Structure-Activity Relationships of N-Benzyl Phenethylamines as 5-HT2A/2C Agonists, ACS Chemical Neuroscience, 2014, pp. 243-249.
Harriott et al., Animal models of migraine and experimental techniques used to examine trigeminal sensory processing, The Journal of Headache and Pain, 2019, 15 pages.
Healthline, How Long Does DMT Last?, Nov. 2019, 12 pages, entire document, especially p. 1 para 1-3. Retrieved om Jun. 24, 2022 from https://www.healthline.com/health/how-long-does-dmt-last.
Huttunen, Prodrugs—from Serendipity to Rational Design, Pharmacological reviews, Sep. 2011, pp. 750-711.
International Search Report and Written Opinion for International Application No. PCT/US2022/026396, dated Jul. 28, 2022, 10 pages.
International Search Report and Written Opinion for International Application No. PCT/US2022/030912, dated Oct. 5, 2022, 20 pages.
International Search Report and Written Opinion for International Application No. PCT/US2022/032918, dated Oct. 12, 2022, 10 pages.
International Search Report and Written Opinion for International Application No. PCT/US2022/045336 dated Jan. 13, 2023, 14 pages.
Invitation to Pay Fee for International Application No. PCT/US2022/082465 dated Mar. 16, 2023, 3 pages.
Kaminska et al., 25C-NBOMe short characterization, Forensic Toxicology, 2020, pp. 490-495.
Klein, et al., Structure-Activity Relationships in Potentially Hallucinogenic N,N-Dialkyltryptamines Substituted in the Benzene Moiety, J. Med. Chen, 1982, pp. 908-913.
Klein et al., Toward selective drug development for the human 5-hydroxytryptamine 1E receptor: a comparison of 5-hydroxytryptamine 1E and 1F receptor structure-affinity relationships, The Journal of Pharmacology and Experimental Therapeutics, 2011, pp. 860-867.
Kraehenmann et al., Dreamlike effects of LSD on waking imagery in humans depend on serotonin 2A receptor activation, Psychopharmacology, 2017, pp. 2031-2046.

(56) References Cited

OTHER PUBLICATIONS

Kraehenmann et al., LSD Increases Primary Process Thinking via Serotonin 2A Receptor Activation, Front. Pharmacol., 2017, 9 pages.

Kucklander, et al., Darstellung und Oxidation von 2-(2, 5-Dihydroxyphenyl)-ethylamin-Derivaten, II/Synthesis and Oxidation of 2-(2, 5-Dihydroxyphenyl)-ethylamine Derivatives, II. Zeitschrift für Naturforschung B, 1987, pp. 1567-1577 (with English abstract).

Li et al., Treatment of breast and lung cancer cells with a N-7 benzyl guanosine monophosphate tryptamine phosphoramidate pronucleotide (4Ei-1) results in chemosensitization to gemcitabine and induced eIF4E proteasomal degradation, Mol Pharm., Feb. 2013, pp. 523-531.

Lima da Cruz et al., Corrigendum: A Single Dose of 5-MeO-DMT Stimulates Cell Proliferation, Neuronal Survivability, Morphological and Functional Changes in Adult Mice Ventral Dentate Gyrus, Front. Mol. Neurosci., 2018, 11 pages.

Lyon et al., Indolealkylamine analogs share 5-HT2 binding characteristics with phenylalkylamine hallucinogens, European Journal of Pharmacology, 1988, pp. 291-297.

Madsen et al., Psilocybin-induced reduction in chronic cluster headache attack frequency correlates with changes in hypothalamic functional connectivity, Neuropsychopharmacology, 2019, pp. 1328-1334.

Madsen et al., Psychedelic effects of psilocybin correlate with serotonin 2A receptor occupancy and plasma psilocin levels, Neuropsychopharmacology, 2019, pp. 1328-1334.

McBride, Bufotenine: Toward an Understanding of Possible Psychoactive Mechanisms, Journal of Psychoactive Drugs, Jul.-Sep. 2000, pp. 321-331.

Melting Point Determination, Melting Range , 2012, 4 pages.

Milne et al., Metabolic engineering of *Saccharomyces cerevisiae* for the de novo production of psilocybin and related tryptamine derivatives, Metabolic Engineering, Jul. 2020, pp. 25-36.

Mithoefer et al., The safety and efficacy of±3, 4-methylenedioxymethamphetamine-assisted psychotherapy in subjects with chronic, treatment-resistant posttraumatic stress disorder: the first randomized controlled pilot study, Journal of Psychopharmacology, Apr. 2010, pp. 439-452.

Nichols, Hallucinogens, Pharmacol. Ther., 2004, pp. 131-181.

Nichols, Structure-Activity Relationships of Phenethylamine Hallucinogens, J. Pharm. Sciences, 1981, pp. 839-849.

Ott, Pharmepena-psychonautics: human intranasal, sublingual and oral pharmacology of 5-methoxy-N, N-dimethyl-tryptamine, Journal of Psychoactive Drugs, Dec. 2001, pp. 403-407.

Ott, J., Pharmañopo-Psychonautics: Human intranasal, sublingual, intrarectal, pulmonary and oral pharmacology of bufotenine, Journal of Psychoactive Drugs, Sep. 2001, pp. 273-281.

Pokorny et al., Modulatory effect of the 5-HT1A agonist buspirone and the mixed non-hallucinogenic 5-HT1A/2A agonist ergotamine on psilocybin-induced psychedelic experience, Eur. Neuropsychopharmacol., Apr. 2016, pp. 756-766.

Pottie, et al., Identification of psychedelic new psychoactive substances (NPS) showing biased agonism at the 5-HT2AR through simultaneous use of β-arrestin 2 and miniGαq bioassays, Biochemical pharmacology, Dec. 2020, 38 pages.

Preller et al., Effects of serotonin 2A/1A receptor stimulation on social exclusion processing, PNAS, May 2016, pp. 5119-5124.

Preller et al., "Role of the 5-HT2A Receptor in Self- and Other-Initiated Social Interaction in Lysergic Acid Diethylamide-Induced States: A Pharmacological fMRI Study," J. Neurosci., Apr. 2018, pp. 3603-3611.

Preller et al., The Fabric of Meaning and Subjective Effects in LSD-Induced States Depend on Serotonin 2A Receptor Activation, Current Biology, Feb. 2017, pp. 451-457.

PubChem SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.

Pubchem, SID 627609, Sep. 2004, 8 pages. Retrieved from the Internet: https://pubchem.ncbi.nlm.nih.gov/substance/627609.

PubChem-SID-310331158, Modify Date: Feb. 15, 2015, p. 2.

PubChem-SID-369863280, Modify Date: May 25, 2018, p. 2.

Puledda et al., "An update on migraine: current understanding and future directions," J Neurol., 2017, pp. 2031-2039.

Ray, "Psychedelics and the Human Receptorome," PloS One, 2010, 17 pages.

Roth et al., "High-affinity Agonist Binding Is Not Sufficient for Agonist Efficacy at 5-Hydroxytryptamine2A Receptors: Evidence in ‚Favor of a Modified Ternary Complex Model," The Journal of Pharmacology and Experimental Therapeautics, 1997, pp. 576-583.

Sargent et al., "Radiohalogen-Labeled Imaging Agents. 3. Compounds for Measurement of Brain Blood Flow by Emission Tomography," Journal of Medicinal Chemistry, 1984, pp. 1071-1077.

Schifano et al., "New psychoactive substances (NPS) and serotonin syndrome onset: A systematic review," Experimental Neurology, Author manuscript, 2021, 29 pages.

Shen et al., "Psychedelic 5-Methoxy-N,N-dimethyltryptamine: Metabolism, Pharmacokinetics, Drug Interactions, and Pharmacological Actions," Curr Drug Metab., Oct. 2010, pp. 659-666.

Sherwood, et al., "Synthesis and Characterization of 5-MeO-DMT Succinate for Clinical Use", Dec. 2020, ACS Omega 2020, pp. 32067-32075. https://doi.org/10.1021/acsomega.0c05099; entire document, especially abstract.

Sigma Succinic acid—Butanedioic acid, 2023, 4 pages.

Substance Record for SID 433987242 to PubChem (hereinafter, "PubChem '242"), Sep. 2020, 7 pages.

The product Item No. 33586 of Cayman Chemical, Apr. 2021, 1 page.

Tirapegui et al., "Synthesis of N-(halogenated) benzyl analogs of superpotent serotonin ligands," J. Chil. Chem. Soc., 2014, pp. 2625-2627.

Titeler et al., "Radioligand binding evidence implicates the brain 5-HT2 receptor as a site of action for LSD and phenylisopropylamine hallucinogens," Psychopharmacology, 1988, pp. 213-216.

Tomaszewski et al., "Benzofuran Bioisosteres of Hallucinogenic Tryptamines," J. Med. Chem., 1992, pp. 2061-2064.

United States Patent and Trademark Office, International Search Report and Written Opinion for International Application No. PCT/US2022/032715 dated Nov. 17, 2022, 18 pages.

United States Patent and Trademark Office, International Search Report and Written Opinion for PCT/US2022/45336, dated Jan. 13, 2023, 14 pages.

United States Patent and Trademark Office, International Search Report and Written Opinion for International Application No. PCT/US2022/082465 dated Jun. 6, 2023, 11 pages.

Uthaug et al., "A single inhalation of vapor from dried toad secretion containing 5-methoxy-N, N-dimethyltryptamine (5-MeO-DMT) in a naturalistic setting is related to sustained enhancement of satisfaction with life, mindfulness-related capacities, and a decrement of psychopathological symptoms," Psychopharmacology, 2019, pp. 2653-2666.

Uthaug et al., "Prospective examination of synthetic 5-methoxy-N,N-dimethyltryptamine inhalation: effects on salivary IL-6, cortisol levels, affect, and non-judgment," Psychopharmacology, 2020, pp. 773-785.

Valle et al., "Inhibition of alpha oscillations through serotonin-2A receptor activation underlies the visual effects of ayahuasca in humans," Author-edited version, 23 pages Eur. Neuropsychopharm, 2016, pp. 1161-1175.

Vollenweider et al., "Psilocybin induces schizophrenia-like psychosis in humans via a serotonin-2 agonist action," Neuroreport, 1998, pp. 3897-3902.

Vollenweider et al., "Psychedelic drugs: neurobiology and potential for treatment of psychiatric disorders," Nature Reviews Neuroscience, Nov. 2020, pp. 611-624.

Wang et al., "Anti-inflammatory and analgesic actions of bufotenine through inhibiting lipid metabolism pathway," Biomedicine & Pharmacotherapy, 2021, 11 pages.

Wey, Structure-based design, synthesis, and biological evaluation of indomethacin derivatives as cyclooxygenase-2 inhibiting nitric oxide donors, Journal of medicinal chemistry, Dec. 2007, pp. 6367-6382.

(56) References Cited

OTHER PUBLICATIONS

Wikipedia, "Perfusion", Dec. 29, 2020, 5 pages. Retrieved on Jun. 24, 2022 from https://en.wikipedia.org/w/index.php?title=Perfusion&oldid=996968059; entire document, especially p. 1 para 1.
Winter et al., Psilocybin-induced stimulus control in the rat Pharmacol. Biochem. Behav., 2007, pp. 472-480.
Winter et al., "The Paradox of 5-Methoxy-N, N-Dimethyltryptamine: An Indoleamine Hallucinogen That Induces Stimulus Control Via 5-HT1A Receptors," Pharmacology Biochemistry and Behavior, 2000, pp. 75-82.
Wood et al., "Prevalence of use and acute toxicity associated with the use of NBOMe drugs," Clinical Toxicology, 2015, pp. 85-92.
Yu, "Indolealkylamines: Biotransformations and Potential Drug-Drug Interactions," The AAPS Journal, Jun. 2008, pp. 242-253.
Berge, S. M., et al., "Pharmaceutical salts", J Pharm Sci. Jan. 1977; 66(1): 1-19.
Carhart-Harris et al., "The Therapeutic Potential of Psychedelic Drugs: Past, Present and Future", Neuropsychopharmacology. Oct. 2017; 42(11): 2105-2113. Epub Apr. 26, 2017.
Co-pending U.S. Appl. No. 18/192,603, inventors Rao; Srinivas G. et al., filed on Mar. 29, 2023.
Co-pending U.S. Appl. No. 18/299,347, inventors Perni; Robert B. et al., filed Apr. 12, 2023.

Davis, et al., "The epidemiology of 5-methoxy-N, N-dimethyltryptamine (5-MeO-DMT) use: Benefits, consequences, patterns of use, subjective effects, and reasons for consumption", J Psychopharmacol, Jul. 2018; 32(7): 779-792. Epub Apr. 30, 2018.
Invitation to Pay Additional Fees for International Application No. PCT/US2022/030912, dated Jul. 28, 2022, 8 pages.
Invitation to Pay Additional Fees for International Application No. PCT/US2022/032918, dated Aug. 12, 2022, 2 pages.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Ruiz et al., "Routes of Drug Administration: Dosage, Design, and Pharmacotherapy Success", Routes of Drug Administration, Chapter 6, Jan. 2018, 43 pages.
Schindler et al., "Exploratory Controlled Study of the Migraine-Suppressing Effects of Psilocybin", Neurotherapeutics, Jan. 2021; 18(1): 534-543. Epub Nov. 12, 2020.
Strassman, "Dose-response study of N, N-dimethyltryptamine in humans: II. Subjective effects and preliminary results of a new rating scale", Archives of general psychiatry, Feb. 1994, pp. 98-108.
Third Party Observation received for International Application No. PCT/US2022/045336, filed May 24, 2023, 8 pages.

\* cited by examiner

DIMETHYLTRYPTAMINE ANALOGUES AS NITRIC OXIDE DELIVERY DRUGS

CROSS-REFERENCE TO RELATED APPLICATION

The present application claims the benefit of priority to U.S. Provisional Application No. 63/295,199, filed Dec. 30, 2021, the contents of which are hereby incorporated by reference in its entirety.

BRIEF SUMMARY OF THE INVENTION

In embodiments, the present disclosure provides dimethyltryptamine derivatives that release nitric oxide (NO) in vivo.

In embodiments, the present disclosure provides prodrugs of dimethyltryptamine and derivatives thereof.

In embodiments, the present disclosure provides compounds of Formula (I), Formula (II), or pharmaceutically acceptable salts thereof.

In embodiments, the present disclosure provides a compound of Formula (I):

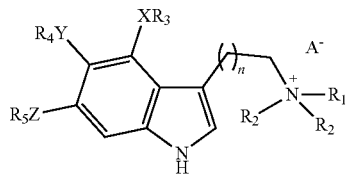

or a pharmaceutically acceptable salt thereof; wherein,
$R_1$, $R_3$, $R_4$ and $R_5$ are independently H, halogen, $C_1$-$C_6$ alkyl, —(C=O)($CR_7R_7'$)$_n$—$ONO_2$, or —(C=O)($CR_7R_7'$)$_m$—CH($NH_2$)$CH_2ONO_2$;
each $R_2$ is independently $C_1$-$C_6$ alkyl;
X, Y, and Z are independently absent, H, O, S, NH and —O—(P=O)OHO—;
$R_7$ and $R_7'$ are independently H, halogen, or $C_1$-$C_6$ alkyl;
m is 2, 3, or 4;
each n is independently 1, 2, 3, 4 or 5; and
$A^-$ is a pharmaceutically acceptable anion,
wherein at least one of $R_1$, $R_3$, $R_4$ and $R_5$ are —(C=O)($CR_7R_7'$)$_n$—$ONO_2$ or —(C=O)($CR_7R_7'$)$_m$—CH($NH_2$)$CH_2ONO_2$.

In embodiments, the present disclosure provides a compound of Formula (II):

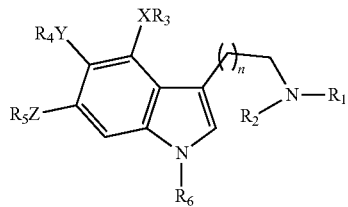

or a pharmaceutically acceptable salt thereof; wherein,
$R_3$, $R_4$, and $R_5$ are independently H, halogen, $C_1$-$C_6$ alkyl, —(C=O)($CR_7R_7'$)$_n$—$ONO_2$, —(C=O)($CR_7R_7'$)$_m$—CH($NH_2$)$CH_2ONO_2$;
$R_1$ and $R_6$ are independently H, $C_1$-$C_6$ alkyl, —(C=O)($CH_2$)$_l$—$ONO_2$; —(C=O)($CH_2$)$_m$—CH($NH_2$)$CH_2ONO_2$;
$R_2$ is H or $C_1$-$C_6$ alkyl;
$R_7$ and $R_7'$ are independently H, halogen, or $C_1$-$C_6$ alkyl;
X, Y, and Z are independently absent, O, S, NH and —O—(P=O)OHO—,
m is 2, 3, or 4; and
each n is independently 1, 2, 3, 4 or 5;
wherein at least one of $R_1$, $R_3$, $R_4$, $R_5$ and $R_6$ is —(C=O)($CR_7R_7'$)$_n$—$ONO_2$, —(C=O)($CR_7R_7'$)$_m$—CH($NH_2$)$CH_2ONO_2$.

In embodiments, the present disclosure provides a pharmaceutical composition, comprising a compound of the present disclosure (e.g., compounds of Formula (I), (II) or Table 1) and a pharmaceutically acceptable excipient.

In embodiments, the present disclosure provides methods of using one or more compounds of the present disclosure (e.g., compounds of Formula (I), (II) or Table 1), e.g., as NO delivery agents.

DETAILED DESCRIPTION OF THE INVENTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to administering a compound or pharmaceutically acceptable salt of the compound or a composition or formulation comprising the compound or pharmaceutically acceptable salt of the compound to a patient.

The term "treating" as used herein with regard to a patient or subject, refers to improving at least one symptom of the patient's or subject's disorder. In some embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

The term "substituted" used herein means any of the groups described herein (e.g., alkyl, alkenyl, alkynyl, alkoxy, aryl, cycloalkyl, cycloalkenyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Compounds

In embodiments, the present disclosure provides dimethyltryptamine derivatives that release nitric oxide (NO) in vivo. In embodiments, the present disclosure provides prodrugs of dimethyltryptamine and derivatives thereof. In embodiments, the present disclosure provides compound of Formula (I) and (II), or pharmaceutically acceptable salts thereof.

In embodiments, the present disclosure provides a compound of Formula (I):

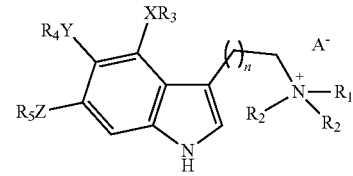

or a pharmaceutically acceptable salt thereof; wherein,
$R_1$, $R_3$, $R_4$ and $R_5$ are independently H, halogen, $C_1$-$C_6$ alkyl, —(C=O)($CR_7R_7'$)$_n$—$ONO_2$, or —(C=O)($CR_7R_7'$)$_m$—CH(NH$_2$)CH$_2$ONO$_2$;
$R_2$ is independently $C_1$-$C_6$ alkyl;
X, Y, and Z are independently absent, H, O, S, NH and —O—(P=O)OHO—;
m is 2, 3, or 4;
each n is independently 1, 2, 3, 4 or 5; and
$A^-$ is a pharmaceutically acceptable anion,
wherein at least one of $R_1$, $R_3$, $R_4$ and $R_5$ are —(C=O)($CR_7R_7'$)$_n$—$ONO_2$ or —(C=O)($CR_7R_7'$)$_m$—CH(NH$_2$)CH$_2$ONO$_2$.

In embodiments of the compounds of Formula (I), $R_1$ is $C_1$-$C_6$ alkyl. In embodiments of the compounds of Formula (I), $R_1$ is methyl, ethyl, or propyl. In embodiments of the compounds of Formula (I), $R_1$ is methyl. In embodiments of the compounds of Formula (I), $R_1$ is H.

In embodiments of the compounds of Formula (I), $R_1$ is $C_1$-$C_6$ alkyl, —(C=O)(CR$_7$R$_7$')$_n$—ONO$_2$, or —(C=O)(CR$_7$R$_7$')$_m$—CH(NH$_2$)CH$_2$ONO$_2$. In embodiments of the compounds of Formula (I), $R_1$ is H, —(C=O)(CR$_7$R$_7$')$_n$—ONO$_2$, or —(C=O)(CR$_7$R$_7$')$_m$—CH(NH$_2$)CH$_2$ONO$_2$. In embodiments of the compounds of Formula (I), $R_1$ is H, $C_1$-$C_6$ alkyl, or —(C=O)(CR$_7$R$_7$')$_m$—CH(NH$_2$)CH$_2$ONO$_2$. In embodiments of the compounds of Formula (I), $R_1$ is H, $C_1$-$C_6$ alkyl, or —(C=O)(CR$_7$R$_7$')$_n$—ONO$_2$. In embodiments of the compounds of Formula (I), $R_1$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (I), $R_1$ is $C_1$-$C_6$ alkyl or —(C=O)(CR$_7$R$_7$')$_m$—CH(NH$_2$)CH$_2$ONO$_2$. In embodiments of the compounds of Formula (I), $R_1$ is halogen, $C_1$-$C_6$ alkyl, —(C=O)(CR$_7$R$_7$')$_n$—ONO$_2$, or —(C=O)(CR$_7$R$_7$')$_m$—CH(NH$_2$)CH$_2$ONO$_2$.

In embodiments of the compounds of Formula (I), $R_1$ is —(C=O)(CR$_7$R$_7$')$_n$—ONO$_2$. In embodiments of the compounds of Formula (I), $R_1$ is —(C=O)(CR$_7$R$_7$')$_m$—CH(NH$_2$)CH$_2$ONO$_2$. In embodiments of the compounds of Formula (I), $R_1$ is —(C=O)(CH$_2$)$_n$—ONO$_2$. In embodiments of the compounds of Formula (I), $R_1$ is —(C=O)(CH$_2$)$_m$—CH(NH$_2$)CH$_2$ONO$_2$. In embodiments of the compounds of Formula (I), $R_1$ is —(C=O)(CH$_2$)$_3$—ONO$_2$. In embodiments of the compounds of Formula (I), $R_1$ is —(C=O)(CH$_2$)$_2$—CH(NH$_2$)CH$_2$ONO$_2$.

In embodiments of the compounds of Formula (I), $R_3$ is H. In embodiments of the compounds of Formula (I), $R_3$ is halogen. In embodiments of the compounds of Formula (I), $R_3$ is $C_1$-$C_6$ alkyl.

In embodiments of the compounds of Formula (I), $R_3$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_3$ is H, halogen, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_3$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (I), $R_3$ is H, halogen, $C_1$-$C_6$ alkyl, or —(C=O)(CR$_7$R$_7$')$_n$—ONO$_2$. In embodiments of the compounds of Formula (I), $R_3$ is H, halogen, or $C_1$-$C_6$ alkyl. In embodiments of the compounds of Formula (I), $R_3$ is H or halogen. In embodiments of the compounds of Formula (I), $R_3$ is H or $C_1$-$C_6$ alkyl. In embodiments of the compounds of Formula (I), $R_3$ is halogen or $C_1$-$C_6$ alkyl.

In embodiments of the compounds of Formula (I), $R_3$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (I), $R_3$ is —(C=O)(CR$_7$R$_7$')$_n$—ONO$_2$. In embodiments of the compounds of Formula (I), $R_3$ is —(C=O)(CR$_7$R$_7$')$_m$—CH(NH$_2$)CH$_2$ONO$_2$.

In embodiments of the compounds of Formula (I), $R_4$ is H, halogen, or $C_1$-$C_6$ alkyl. In embodiments of the compounds of Formula (I), $R_4$ is H or halogen. In embodiments of the compounds of Formula (I), $R_4$ is H or $C_1$-$C_6$ alkyl. In embodiments of the compounds of Formula (I), $R_4$ is halogen or $C_1$-$C_6$ alkyl.

In embodiments of the compounds of Formula (I), $R_4$ is halogen, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_4$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_4$ is H, halogen, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_4$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (I), $R_4$ is H, halogen, $C_1$-$C_6$ alkyl, or —(C=O)(CR$_7$R$_7$')$_n$—ONO$_2$.

In embodiments of the compounds of Formula (I), $R_4$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (I), $R_4$ is —(C=O)(CR$_7$R$_7$')$_n$—ONO$_2$. In embodiments of the compounds of Formula (I), $R_4$ is —(C=O)(CR$_7$R$_7$')$_m$—CH(NH$_2$)CH$_2$ONO$_2$.

In embodiments of the compounds of Formula (I), $R_5$ is H. In embodiments of the compounds of Formula (I), $R_5$ is halogen. In embodiments of the compounds of Formula (I), $R_5$ is $C_1$-$C_6$ alkyl. In embodiments of the compounds of Formula (I), $R_5$ is H, halogen, or $C_1$-$C_6$ alkyl.

In embodiments of the compounds of Formula (I), $R_5$ is H or halogen. In embodiments of the compounds of Formula (I), $R_5$ is H or $C_1$-$C_6$ alkyl. In embodiments of the compounds of Formula (I), $R_5$ is halogen or $C_1$-$C_6$ alkyl.

In embodiments of the compounds of Formula (I), $R_5$ is halogen, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_5$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_5$ is H, halogen, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (I), $R_5$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (I), $R_5$ is H, halogen, $C_1$-$C_6$ alkyl, or —(C=O)(CR$_7$R$_7$')$_n$—ONO$_2$.

In embodiments of the compounds of Formula (I), $R_5$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (I), $R_5$ is —(C=O)(CR$_7$R$_7$')$_n$—ONO$_2$. In embodiments of the compounds of Formula (I), $R_5$ is —(C=O)(CR$_7$R$_7$')$_m$—CH(NH$_2$)CH$_2$ONO$_2$.

In embodiments of the compounds of Formula (I), $R_7$ and $R_7$' independently H or $C_1$-$C_6$ alkyl. In embodiments of the compounds of Formula (I), $R_7$ and $R_7$' independently H or $C_1$-$C_3$ alkyl. In embodiments of the compounds of Formula (I), $R_7$ and $R_7$' independently H or halogen alkyl. In embodiments of the compounds of Formula (I), $R_7$ and $R_7$' independently halogen or $C_1$-$C_6$ alkyl. In embodiments of the compounds of Formula (I), $R_7$ and $R_7$' independently halogen or $C_1$-$C_3$ alkyl.

In embodiments of the compounds of Formula (I), X is O, S, NH and —O—(P=O)OHO—. In embodiments of the compounds of Formula (I), X is absent, S, NH and —O—(P=O)OHO—. In embodiments of the compounds of Formula (I), X is absent, O, S or —O—(P=O)OHO—. In embodiments of the compounds of Formula (I), X is absent, O, S, or NH. In embodiments of the compounds of Formula (I), X is O or —O—(P=O)OHO—.

In embodiments of the compounds of Formula (I), X is absent. In embodiments of the compounds of Formula (I), X is O. In embodiments of the compounds of Formula (I), X is S. In embodiments of the compounds of Formula (I), X is NH. In embodiments of the compounds of Formula (I), X is —O—(P=O)OHO—.

In embodiments of the compounds of Formula (I), Y is O, S, NH and —O—(P═O)OHO—. In embodiments of the compounds of Formula (I), Y is absent, S, NH and —O—(P═O)OHO—. In embodiments of the compounds of Formula (I), Y is absent, O, S or —O—(P═O)OHO—. In embodiments of the compounds of Formula (I), Y is absent, O, S, or NH. In embodiments of the compounds of Formula (I), Y is O or —O—(P═O)OHO—.

In embodiments of the compounds of Formula (I), Y is absent. In embodiments of the compounds of Formula (I), Y is O. In embodiments of the compounds of Formula (I), Y is S. In embodiments of the compounds of Formula (I), Y is NH. In embodiments of the compounds of Formula (I), Y is —O—(P═O)OHO—.

In embodiments of the compounds of Formula (I), Z is O, S, NH and —O—(P═O)OHO—. In embodiments of the compounds of Formula (I), Z is absent, S, NH and —O—(P═O)OHO—. In embodiments of the compounds of Formula (I), Z is absent, O, S or —O—(P═O)OHO—. In embodiments of the compounds of Formula (I), Z is absent, O, S, or NH. In embodiments of the compounds of Formula (I), Z is O or —O—(P═O)OHO—.

In embodiments of the compounds of Formula (I), Z is absent. In embodiments of the compounds of Formula (I), Z is O. In embodiments of the compounds of Formula (I), Z is S. In embodiments of the compounds of Formula (I), Z is NH. In embodiments of the compounds of Formula (I), Z is —O—(P═O)OHO—.

In embodiments of the compounds of Formula (I), n is 1. In embodiments of the compounds of Formula (I), n is 2. In embodiments of the compounds of Formula (I), n is 3. In embodiments of the compounds of Formula (I), n is 4. In embodiments of the compounds of Formula (I), n is 5.

In embodiments of the compounds of Formula (I), m is 2. In embodiments of the compounds of Formula (I), m is 3. In embodiments of the compounds of Formula (I), m is 4. In embodiments of the compounds of Formula (I), m is 5.

In embodiments of the compounds of Formula (I), $R_3$ is H and X is absent. In embodiments of compounds of Formula (I), $R_3$ is halogen and X is absent. In embodiments of compounds of Formula (I), $R_3$ is H and X is O. In embodiments of compounds of Formula (I), $R_3$ is $C_1$-$C_6$ alkyl and X is O. In embodiments of compounds of Formula (I), $R_3$ is $C_1$, F, Br, or I and X is absent. In embodiments of compounds of Formula (I), $R_3$ is F and X is absent.

In embodiments of the compounds of Formula (I), $R_4$ is H and Y is absent. In embodiments of compounds of Formula (I), $R_4$ is halogen and Y is absent. In embodiments of compounds of Formula (I), $R_4$ is H and Y is O. In embodiments of compounds of Formula (II), $R_4$ is $C_1$-$C_6$ alkyl and Y is O. In embodiments of compounds of Formula (I), $R_4$ is $C_1$, F, Br, or I and Y is absent. In embodiments of compounds of Formula (I), $R_4$ is F and Y is absent.

In embodiments of the compounds of Formula (I), $R_5$ is H and Z is absent. In embodiments of compounds of Formula (I), $R_5$ is halogen and Z is absent. In embodiments of compounds of Formula (I), $R_5$ is H and Z is O. In embodiments of compounds of Formula (I), $R_5$ is $C_1$-$C_6$ alkyl and Z is O. In embodiments of compounds of Formula (I), $R_5$ is $C_1$, F, Br, or I and Z is absent. In embodiments of compounds of Formula (II), $R_5$ is F and Z is absent.

Formula (II):
In embodiments, provided herein is a compound of Formula (II):

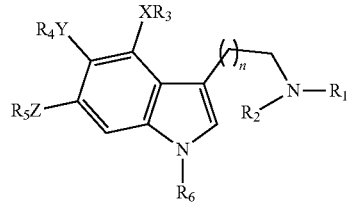

or a pharmaceutically acceptable salt thereof; wherein,
$R_3$, $R_4$, and $R_5$ are independently H, halogen, $C_1$-$C_6$ alkyl, —(C═O)(CR$_7$R$_7$')$_n$—ONO$_2$, or —(C═O)(CR$_7$R$_7$')$_m$—CH(NH$_2$)CH$_2$ONO$_2$;
$R_1$ and $R_6$ are independently H, $C_1$-$C_6$ alkyl, —(C═O)(CR$_7$R$_7$')$_n$—ONO$_2$, or —(C═O)(CR$_7$R$_7$')$_m$—CH(NH$_2$)CH$_2$ONO$_2$;
$R_2$ is H or $C_1$-$C_6$ alkyl; and
$R_7$ and $R_7$' are independently H, halogen, or $C_1$-$C_6$ alkyl;
X, Y, and Z are independently absent, O, S, NH and —O—(P═O)OHO—,
m is 2, 3, or 4; and
each n is independently 1, 2, 3, 4 or 5;
wherein at least one of $R_1$, $R_3$, $R_4$, $R_5$ and $R_6$ is —(C═O)(CR$_7$R$_7$')$_n$—ONO$_2$, —(C═O)(CR$_7$R$_7$')$_m$—CH(NH$_2$)CH$_2$ONO$_2$.

In embodiments of the compounds of Formula (II), $R_1$ is $C_1$-$C_6$ alkyl. In embodiments of the compounds of Formula (II), $R_1$ is methyl, ethyl, or propyl. In embodiments of the compounds of Formula (II), $R_1$ is methyl. In embodiments of the compounds of Formula (II), $R_1$ is H.

In embodiments of the compounds of Formula (II), $R_1$ is —(C═O)(CR$_7$R$_7$')$_n$—ONO$_2$.

In embodiments of the compounds of Formula (II), $R_1$ is —(C═O)(CR$_7$R$_7$')$_m$—CH(NH$_2$)CH$_2$ONO$_2$. In embodiments of the compounds of Formula (II), $R_1$ is —(C═O)(CH$_2$)$_n$—ONO$_2$. In embodiments of the compounds of Formula (II), $R_1$ is —(C═O)(CH$_2$)$_m$—CH(NH$_2$)CH$_2$ONO$_2$. In embodiments of the compounds of Formula (II), $R_1$ is —(C═O)(CH$_2$)$_3$—ONO$_2$. In embodiments of the compounds of Formula (II), $R_1$ is —(C═O)(CH$_2$)$_2$—CH(NH$_2$)CH$_2$ONO$_2$.

In embodiments of the compounds of Formula (II), $R_1$ is $C_1$-$C_6$ alkyl, —(C═O)(CR$_7$R$_7$')$_n$—ONO$_2$, or —(C═O)(CR$_7$R$_7$')$_m$—CH(NH$_2$)CH$_2$ONO$_2$. In embodiments of the compounds of Formula (II), $R_1$ is H, —(C═O)(CR$_7$R$_7$')$_n$—ONO$_2$, or —(C═O)(CR$_7$R$_7$')$_m$—CH(NH$_2$)CH$_2$ONO$_2$. In embodiments of the compounds of Formula (II), $R_1$ is H, $C_1$-$C_6$ alkyl, or —(C═O)(CR$_7$R$_7$')$_m$—CH(NH$_2$)CH$_2$ONO$_2$. In embodiments of the compounds of Formula (II), $R_1$ is H, $C_1$-$C_6$ alkyl, or —(C═O)(CR$_7$R$_7$')$_n$—ONO$_2$. In embodiments of the compounds of Formula (II), $R_1$ is —(C═O)(CR$_7$R$_7$')$_n$—ONO$_2$ or —(C═O)(CR$_7$R$_7$')$_m$—CH(NH$_2$)CH$_2$ONO$_2$. In embodiments of the compounds of Formula (II), $R_1$ is $C_1$-$C_6$ alkyl or —(C═O)(CR$_7$R$_7$')$_m$—CH(NH$_2$)CH$_2$ONO$_2$. In embodiments of the compounds of Formula (II), $R_1$ is $C_1$-$C_6$ alkyl, or —(C═O)(is halogen, $C_1$-$C_6$ alkyl, —(C═O)(CR$_7$R$_7$')$_n$—ONO$_2$, —(C═O)(CR$_7$R$_7$')$_m$—CH(NH$_2$)CH$_2$ONO$_2$.

In embodiments of the compounds of Formula (II), $R_3$ is H, halogen, or $C_1$-$C_6$ alkyl. In embodiments of the compounds of Formula (II), $R_3$ is H or halogen. In embodiments of the compounds of Formula (II), $R_3$ is H or $C_1$-$C_6$ alkyl. In embodiments of the compounds of Formula (II), $R_3$ is halogen or $C_1$-$C_6$ alkyl. In embodiments of the compounds of Formula (II), $R_3$ is H. In embodiments of the compounds of Formula (II), $R_3$ is halogen. In embodiments of the compounds of Formula (II), $R_3$ is $C_1$-$C_6$ alkyl.

In embodiments of the compounds of Formula (II), $R_3$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_3$ is H, halogen, —(C=O)(CR$_7$R$_7$')$_n$—ONO$_2$, —(C=O)(CR$_7$R$_7$')$_m$—CH(NH$_2$)CH$_2$ONO$_2$.

In embodiments of the compounds of Formula (II), $R_3$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (II), $R_3$ is H, halogen, $C_1$-$C_6$ alkyl, or —(C=O)(CR$_7$R$_7$')$_n$—ONO$_2$. In embodiments of the compounds of Formula (II), $R_3$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (II), $R_3$ is —(C=O)(CR$_7$R$_7$')$_n$—ONO$_2$. In embodiments of the compounds of Formula (II), $R_3$ is —(C=O)(CR$_7$R$_7$')$_m$—CH(NH$_2$)CH$_2$ONO$_2$.

In embodiments of the compounds of Formula (II), $R_4$ is H, halogen, or $C_1$-$C_6$ alkyl. In embodiments of the compounds of Formula (II), $R_4$ is H or halogen. In embodiments of the compounds of Formula (II), $R_4$ is H or $C_1$-$C_6$ alkyl. In embodiments of the compounds of Formula (II), $R_4$ is halogen or $C_1$-$C_6$ alkyl.

In embodiments of the compounds of Formula (II), $R_4$ is halogen, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_4$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_4$ is H, halogen, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_4$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (II), $R_4$ is H, halogen, $C_1$-$C_6$ alkyl, or —(C=O)(CR$_7$R$_7$')$_n$—ONO$_2$. In embodiments of the compounds of Formula (II), $R_4$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (II), $R_4$ is —(C=O)(CR$_7$R$_7$')$_n$—ONO$_2$. In embodiments of the compounds of Formula (II), $R_4$ is —(C=O)(CR$_7$R$_7$')$_m$—CH(NH$_2$)CH$_2$ONO$_2$.

In embodiments of the compounds of Formula (II), $R_5$ is H, halogen, or $C_1$-$C_6$ alkyl. In embodiments of the compounds of Formula (II), $R_5$ is H or halogen. In embodiments of the compounds of Formula (II), $R_5$ is H or $C_1$-$C_6$ alkyl. In embodiments of the compounds of Formula (II), $R_5$ is halogen or $C_1$-$C_6$ alkyl. In embodiments of the compounds of Formula (II), $R_5$ is H. In embodiments of the compounds of Formula (II), $R_5$ is halogen. In embodiments of the compounds of Formula (II), $R_5$ is $C_1$-$C_6$ alkyl.

In embodiments of the compounds of Formula (II), $R_5$ is halogen, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_5$ is H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_5$ is H, halogen, —(C=O)(CR$_7$R$_7$')$_n$—ONO$_2$, —(C=O)(CR$_7$R$_7$')$_m$—CH(NH$_2$)CH$_2$ONO$_2$. In embodiments of the compounds of Formula (II), $R_5$ is H, halogen, $C_1$-$C_6$ alkyl, or —(C=O)(CR$_7$R$_7$')$_m$—CH(NH$_2$)CH$_2$ONO$_2$. In embodiments of the compounds of Formula (II), $R_5$ is H, halogen, $C_1$-$C_6$ alkyl, or —(C=O)(CR$_7$R$_7$')$_n$—ONO$_2$. In embodiments of the compounds of Formula (II), $R_5$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (II), $R_5$ is —(C=O)(CR$_7$R$_7$')$_n$—ONO$_2$. In embodiments of the compounds of Formula (II), $R_5$ is —(C=O)(CR$_7$R$_7$')$_m$—CH(NH$_2$)CH$_2$ONO$_2$.

In embodiments of the compounds of Formula (II), $R_6$ is H or $C_1$-$C_6$ alkyl. In embodiments of the compounds of Formula (II), $R_6$ is $C_1$-$C_6$ alkyl. In embodiments of the compounds of Formula (II), $R_6$ is methyl, ethyl, or propyl. In embodiments of the compounds of Formula (II), $R_6$ is methyl.

In embodiments of the compounds of Formula (II), $R_6$ is H. In embodiments of the compounds of Formula (II), $R_6$ is —(C=O)(CR$_7$R$_7$')$_n$—ONO$_2$.

In embodiments of the compounds of Formula (II), $R_6$ is —(C=O)(CR$_7$R$_7$')$_m$—CH(NH$_2$)CH$_2$ONO$_2$. In embodiments of the compounds of Formula (II), $R_6$ is —(C=O)(CH$_2$)$_n$—ONO$_2$. In embodiments of the compounds of Formula (II), $R_6$ is —(C=O)(CH$_2$)$_m$—CH(NH$_2$)CH$_2$ONO$_2$. In embodiments of the compounds of Formula (II), $R_6$ is —(C=O)(CH$_2$)$_3$—ONO$_2$. In embodiments of the compounds of Formula (II), $R_6$ is —(C=O)(CH$_2$)$_2$—CH(NH$_2$)CH$_2$ONO$_2$. In embodiments of the compounds of Formula (II), $R_6$ is $C_1$-$C_6$ alkyl, —(C=O)(CR$_7$R$_7$')$_n$—ONO$_2$, or —(C=O)(CR$_7$R$_7$')$_m$—CH(NH$_2$)CH$_2$ONO$_2$. In embodiments of the compounds of Formula (II), $R_6$ is H, —(C=O)(CR$_7$R$_7$')$_n$—ONO$_2$, or —(C=O)(CR$_7$R$_7$')$_m$—CH(NH$_2$)CH$_2$ONO$_2$. In embodiments of the compounds of Formula (II), $R_6$ is H, $C_1$-$C_6$ alkyl, or —(C=O)(CR$_7$R$_7$')$_m$—CH(NH$_2$)CH$_2$ONO$_2$. In embodiments of the compounds of Formula (II), $R_6$ is H, $C_1$-$C_6$ alkyl, or —(C=O)(CR$_7$R$_7$')$_n$—ONO$_2$. In embodiments of the compounds of Formula (II), $R_6$ is —(C=O)(CR$_7$R$_7$')$_n$—ONO$_2$ or —(C=O)(CR$_7$R$_7$')$_m$—CH(NH$_2$)CH$_2$ONO$_2$. In embodiments of the compounds of Formula (II), $R_6$ is $C_1$-$C_6$ alkyl or —(C=O)(CR$_7$R$_7$')$_m$—CH(NH$_2$)CH$_2$ONO$_2$.

In embodiments of the compounds of Formula (II), $R_6$ is $C_1$-$C_6$ alkyl, or —(C=O)(CR$_7$R$_7$')$_n$—ONO$_2$. In embodiments of the compounds of Formula (II), $R_6$ is H or —(C=O)(CR$_7$R$_7$')$_n$—ONO$_2$.

In embodiments of the compounds of Formula (II), $R_6$ is H or —(C=O)(CR$_7$R$_7$')$_m$—CH(NH$_2$)CH$_2$ONO$_2$.

In embodiments of the compounds of Formula (II), $R_7$ and $R_7$' independently H or $C_1$-$C_6$ alkyl. In embodiments of the compounds of Formula (II), $R_7$ and $R_7$' independently H or $C_1$-$C_3$ alkyl. In embodiments of the compounds of Formula (II), $R_7$ and $R_7$' independently H or halogen alkyl. In embodiments of the compounds of Formula (II), $R_7$ and $R_7$' independently halogen or $C_1$-$C_6$ alkyl. In embodiments of the compounds of Formula (II), $R_7$ and $R_7$' independently halogen or $C_1$-$C_3$ alkyl.

In embodiments of the compounds of Formula (II), X is O, S, NH and —O—(P=O)OHO—. In embodiments of the compounds of Formula (II), X is absent, S, NH and —O—(P=O)OHO—. In embodiments of the compounds of Formula (II), X is absent, O, S or —O—(P=O)OHO—. In embodiments of the compounds of Formula (II), X is absent, O, S, or NH. In embodiments of the compounds of Formula (II), X is absent. In embodiments of the compounds of Formula (II), X is O. In embodiments of the compounds of Formula (II), X is S. In embodiments of the compounds of Formula (II), X is NH. In embodiments of the compounds of Formula (II), X is —O—(P=O)OHO—. In embodiments of the compounds of Formula (II), X is O or —O—(P=O)OHO—.

In embodiments of the compounds of Formula (II), Y is O, S, NH and —O—(P=O)OHO—. In embodiments of the compounds of Formula (II), Y is absent, S, NH and —O—(P=O)OHO—. In embodiments of the compounds of Formula (II), Y is absent, O, S or —O—(P=O)OHO—. In embodiments of the compounds of Formula (II), Y is absent, O, S, or NH. In embodiments of the compounds of Formula (II), Y is absent. In embodiments of the compounds of Formula (II), Y is O. In embodiments of the compounds of Formula (II), Y is S. In embodiments of the compounds of Formula (II), Y is NH. In embodiments of the compounds of Formula (II), Y is —O—(P=O)OHO—. In embodiments of the compounds of Formula (II), Y is O or —O—(P=O)OHO—.

In embodiments of the compounds of Formula (II), Z is O, S, NH and —O—(P=O)OHO—. In embodiments of the compounds of Formula (II), Z is absent, S, NH and —O—(P=O)OHO—. In embodiments of the compounds of Formula (II), Z is absent, O, S or —O—(P=O)OHO—. In embodiments of the compounds of Formula (II), Z is absent, O, S, or NH. In embodiments of the compounds of Formula (II), Z is absent. In embodiments of the compounds of Formula (II), Z is O. In embodiments of the compounds of Formula (II), Z is S. In embodiments of the compounds of Formula (II), Z is NH. In embodiments of the compounds of Formula (II), Z is —O—(P=O)OHO—. In embodiments of the compounds of Formula (II), Z is O or —O—(P=O)OHO—.

In embodiments of the compounds of Formula (II), n is 1. In embodiments of the compounds of Formula (II), n is 2. In embodiments of the compounds of Formula (II), n is 3. In embodiments of the compounds of Formula (II), n is 4. In embodiments of the compounds of Formula (II), n is 5.

In embodiments of the compounds of Formula (II), m is 2. In embodiments of the compounds of Formula (II), m is 3. In embodiments of the compounds of Formula (II), m is 4. In embodiments of the compounds of Formula (II), m is 5.

In embodiments of the compounds of Formula (II), $R_3$ is H and X is absent. In embodiments of compounds of Formula (II), $R_3$ is halogen and X is absent. In embodiments of compounds of Formula (II), $R_3$ is H and X is O. In embodiments of compounds of Formula (II), $R_3$ is $C_1$-$C_6$ alkyl and X is O. In embodiments of compounds of Formula (II), $R_3$ is $C_1$, F, Br, or I and X is absent. In embodiments of compounds of Formula (II), $R_3$ is F and X is absent.

In embodiments of the compounds of Formula (II), $R_4$ is H and Y is absent. In embodiments of compounds of Formula (II), $R_4$ is halogen and Y is absent. In embodiments of compounds of Formula (II), $R_4$ is H and Y is O. In embodiments of compounds of Formula (II), $R_4$ is $C_1$-$C_6$ alkyl and Y is O. In embodiments of compounds of Formula (II), $R_4$ is $C_1$, F, Br, or I and Y is absent. In embodiments of (compounds of Formula (II), $R_4$ is F and Y is absent.

In embodiments of the compounds of Formula (II), $R_5$ is H and Z is absent. In embodiments of compounds of Formula (II), $R_5$ is halogen and Z is absent. In embodiments of compounds of Formula (II), $R_5$ is H and Z is O. In embodiments of compounds of Formula (II), $R_5$ is $C_1$-$C_6$ alkyl and Z is O. In embodiments of compounds of Formula (II), $R_5$ is $C_1$, F, Br, or I and Z is absent.

In embodiments of compounds of Formula (II), $R_5$ is F and Z is absent.

TABLE 1

| | Compounds of Formula (II) | |
| --- | --- | --- |
| No. | Structure | |
| 2-1 | 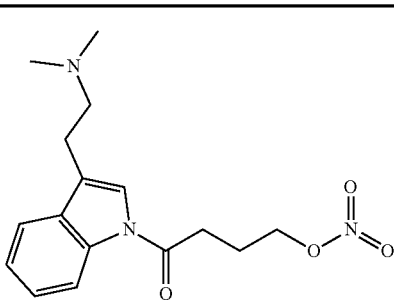 | 4-(3-(2-(dimethylamino)ethyl)-1H-indol-1-yl)-4-oxobutyl nitrate |
| 2-2 | 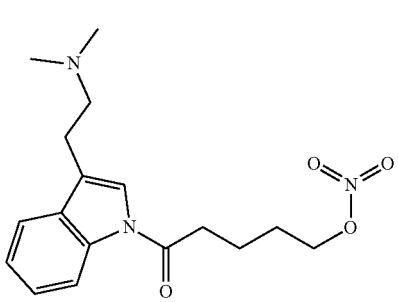 [SMILES: CN(C)CCc1cn(C(=O)CCCCO[N+](=O)[O-])c2ccccc12] | 5-(3-(2-(dimethylamino)ethyl)-1H-indol-1-yl)-5-oxopentyl nitrate |

TABLE 1-continued

| Compounds of Formula (II) | | |
|---|---|---|
| No. | Structure | |
| 2-3 | | 2-(chloro-λ⁵-azaneyl)-5-(3-(2-(dimethylamino)ethyl)-1H-indol-1-yl)-5-oxopentyl nitrate |
| 2-4 | | 2-amino-5-(3-(2-(dimethylamino)ethyl)-1H-indol-1-yl)-5-oxopentyl nitrate |
| 2-5 | | 4-(3-(2-(dimethylamino)ethyl)-5-methoxy-1H-indol-1-yl)-4-oxobutyl nitrate |
| 2-6 | | 4-(3-(2-(dimethylamino)ethyl)-5-fluoro-1H-indol-1-yl)-4-oxobutyl nitrate |
| 2-7 | | 4-(3-(2-(dimethylamino)ethyl)-4-hydroxy-1H-indol-1-yl)-4-oxobutyl nitrate |

TABLE 1-continued

Compounds of Formula (II)

| No. | Structure | Name |
|---|---|---|
| 2-8 | 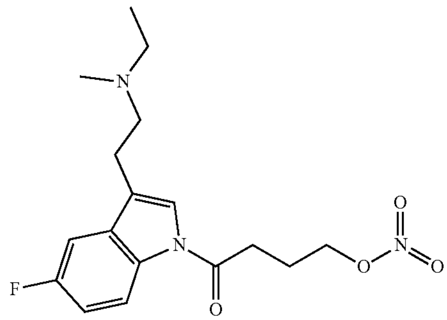 [SMILES: CCN(C)CCc1cn(C(=O)CCCO[N+](=O)[O-])c2ccc(F)cc12] | 4-(3-(2-(ethyl(methyl)amino)ethyl)-5-fluoro-1H-indol-1-yl)-4-oxobutyl nitrate |
| 2-9 | 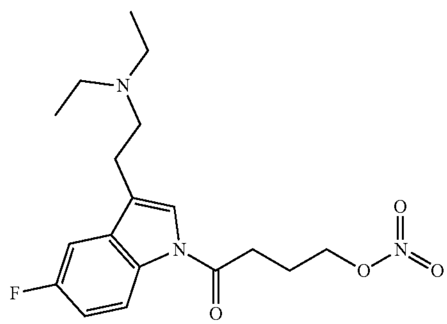 [SMILES: CCN(CC)CCc1cn(C(=O)CCCO[N+](=O)[O-])c2ccc(F)cc12] | 4-(3-(2-(diethylamino)ethyl)-5-fluoro-1H-indol-1-yl)-4-oxobutyl nitrate |
| 2-10 | 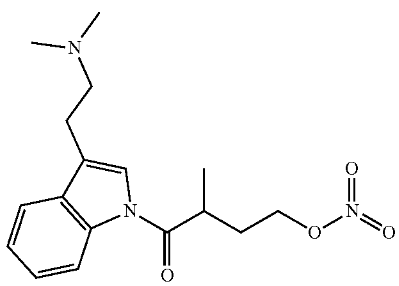 [SMILES: CC(CCO[N+](=O)[O-])C(=O)n1cc(CCN(C)C)c2ccccc21] | 4-(3-(2-(dimethylamino)ethyl)-1H-indol-1-yl)-3-methyl-4-oxobutyl nitrate |
| 2-11 | 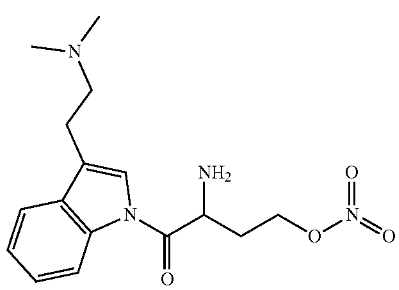 [SMILES: CN(C)CCc1cn(C(=O)C(N)CCO[N+](=O)[O-])c2ccccc12] | 3-amino-4-(3-(2-(dimethylamino)ethyl)-1H-indol-1-yl)-4-oxobutyl nitrate |
| 2-12 | 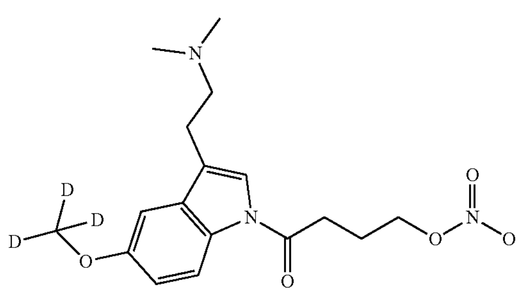 | 4-(3-(2-(dimethylamino)ethyl)-5-(methoxy-$d_3$)-H-indol-1-yl)-4-oxobutyl nitrate |

TABLE 1-continued

Compounds of Formula (II)

| No. | Structure | |
|---|---|---|
| 2-13 | 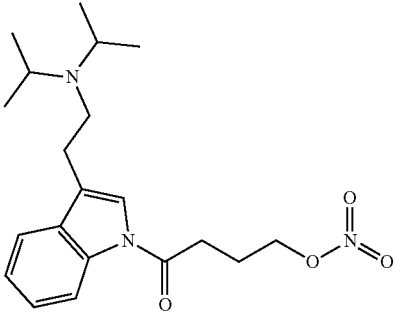 [SMILES: CC(C)N(CCc1cn(C(=O)CCCO[N+](=O)[O-])c2ccccc12)C(C)C] | 4-(3-(2-(diisopropylamino)ethyl)-1H-indol-1-yl)-4-oxobutyl nitrate |
| 2-14 | 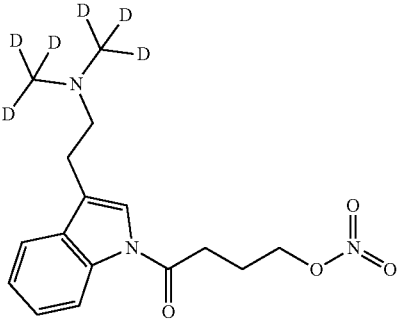 [SMILES: [2H]C([2H])([2H])N(CCc1cn(C(=O)CCCO[N+](=O)[O-])c2ccccc12)C([2H])([2H])[2H]] | 4-(3-(2-(bis(methyl-d3)amino)ethyl)-1H-indol-1-yl)-4-oxobutyl nitrate |

Compositions

In embodiments, the present disclosure provides a pharmaceutical composition comprising a therapeutically effective amount of one or more compounds of the present disclosure (e.g., a compound of Formula (I), (II), or Table 1) or a pharmaceutically acceptable salt thereof and a pharmaceutically acceptable excipient.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods of Treatment

In one aspect, the present disclosure provides methods of treating a disease or disorder in a subject in need thereof, the methods comprising administering a therapeutically effective amount of a compound described herein (e.g., a compound of Formula (I), (II), or Table 1) or pharmaceutically acceptable salt thereof to the subject.

In embodiments, the disease or disorder is a mental health disease or disorder. In embodiments, the mental health disease or disorder is selected from the group consisting of major depressive disorder, treatment resistant depression, substance use disorders and eating disorders.

In embodiments, eating disorders include illnesses such as anorexia nervosa, bulimia nervosa, and other disorders related to eating (e.g., binge eating).

In embodiments, the mental health disease or disorder is an eating disorder.

In embodiments, the mental health disease or disorder is selected from the group consisting of compulsive disorders, anxiety disorders, stress disorders, and rumination.

In embodiments, the mental health disease or disorder is a mood disorder. In embodiments, mood disorders include e.g., depressive disorders, such as major depressive disorder or treatment resistant depression.

In embodiments, the mental health disorder is a substance abuse disorder. In embodiments, substance use related disorders are disorders of maladaptive patterns of substance use, and include criteria, such as recurrent substance use related problems, tolerance to a substance, withdrawal upon discontinuing use, an inability to cut down or control use of the substance, and giving up important social, occupational, or recreational activities because of using the substance. See e.g., the Diagnostic and Statistical Manual of Mental Disorders (DSM-5). In embodiments, the substance use related disorder is a disorder resulting from the use of: alcohol; caffeine; cannabis; hallucinogens (such as phencyclidine or similarly acting arylcyclohexylamines, and other hallucinogens, such as LSD); inhalants; opioids; sedatives, hypnotics, or anxiolytics; stimulants (including amphetamine-type substances, cocaine, and other stimulants); tobacco; and other substances.

In embodiments, administering compounds of the present disclosure (e.g., a compound of Formula (I), (II), or Table 1) or a pharmaceutically acceptable salt thereof releases nitric oxide (NO) (e.g., the compounds of the present disclosure are NO delivery drugs). In embodiments the compounds of the present disclosure are useful for releasing NO in vivo.

Numbered Embodiments

In addition to the disclosure above, the Examples below, and the appended claims, the disclosure sets for the following numbered embodiments.

1. A Compound of Formula (II).

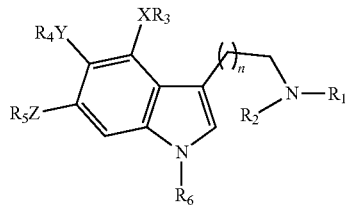

or a pharmaceutically acceptable salt thereof; wherein,
$R_3$, $R_4$, and $R_5$ are independently H, halogen, $C_1$-$C_6$ alkyl, —(C=O)(CR$_7$R$_7$')$_n$—ONO$_2$, or —(C=O)(CR$_7$R$_7$')$_m$—CH(NH$_2$)CH$_2$ONO$_2$;
$R_1$ and $R_6$ are independently H, $C_1$-$C_6$ alkyl, —(C=O)(CR$_7$R$_7$')$_n$—ONO$_2$, —(C=O)(CR$_7$R$_7$')$_m$—CH(NH$_2$)CH$_2$ONO$_2$;
$R_2$ is H or $C_1$-$C_6$ alkyl; and
$R_7$ and $R_7$' are independently H, halogen, or $C_1$-$C_6$ alkyl;
X, Y, and Z are independently absent, O, S, NH, or —O—(P=O)OHO—,
m is 2, 3, or 4; and
each n is independently 1, 2, 3, 4 or 5;
wherein at least one of $R_1$, $R_3$, $R_4$, $R_5$ and $R_6$ is —(C=O)(CR$_7$R$_7$')$_n$—ONO$_2$, —(C=O)(CR$_7$R$_7$')$_m$—CH(NH$_2$)CH$_2$ONO$_2$.

2. The compound of embodiment 1, wherein $R_1$ is $C_1$-$C_6$ alkyl.
3. The compound of embodiment 1, wherein $R_1$ is methyl.
4. The compound of embodiment 1, wherein $R_1$ is H.
5. The compound of any one of embodiments 1-4, wherein $R_2$ is $C_1$-$C_6$ alkyl.
6. The compound of any one of embodiments 1-4 wherein $R_2$ is methyl.
7. The compound of any one of embodiments 1-4, wherein $R_2$ is H.
8. The compound of any one of embodiments 1-7, wherein $R_3$ is H and X is absent.
9. The compound of any one of embodiments 1-7, wherein $R_3$ is halogen and X is absent.
10. The compound of any one of embodiments 1-7, wherein $R_3$ is H and X is O.
11. The compound of any one of embodiments 1-7, wherein $R_3$ is $C_1$-$C_6$ alkyl and X is O.
12. The compound of any one of embodiments 1-11, wherein $R_4$ is H and Y is absent.
13. The compound of any one of embodiments 1-11, wherein $R_4$ is H and Y is O.
14. The compound of any one of embodiments 1-11, wherein $R_4$ is halogen and Y is absent.
15. The compound of any one of embodiments 1-11, wherein $R_4$ is $C_1$-$C_6$ alkyl and Y is O.
16. The compound of any one of embodiments 1-15, wherein $R_5$ is H and Z is absent.
17. The compound of any one of embodiments 1-15, wherein $R_5$ is H and Z is O.
18. The compound of any one of embodiments 1-15, wherein $R_5$ is halogen and Z is absent.
19. The compound of any one of embodiments 1-15, wherein $R_5$ is $C_1$-$C_6$ alkyl and Z is absent.
20. The compound of any one of embodiments 1-15, wherein $R_5$ is $C_1$-$C_6$ alkyl and Z is O.
21. The compound of any one of embodiments 1-20, wherein $R_6$ is —(C=O)(CR$_7$R$_7$')$_n$—ONO$_2$.
22. The compound of any one of embodiments 1-20, wherein $R_6$ is —(C=O)(CR$_7$R$_7$')$_m$—CH(NH$_2$)CH$_2$ONO$_2$.
23. The compound of any one of embodiments 1-20, wherein $R_6$ is —(C=O)(CH$_2$)$_n$—ONO$_2$.
24. The compound of any one of embodiments 1-20, wherein $R_6$ is —(C=O)(CH$_2$)$_m$—CH(NH$_2$)CH$_2$ONO$_2$.
25. The compound of any one of embodiments 1-20, wherein $R_6$ is —(C=O)(CH$_2$)$_3$—ONO$_2$.
26. The compound of any one of embodiments 1-25, having the following chemical formula:

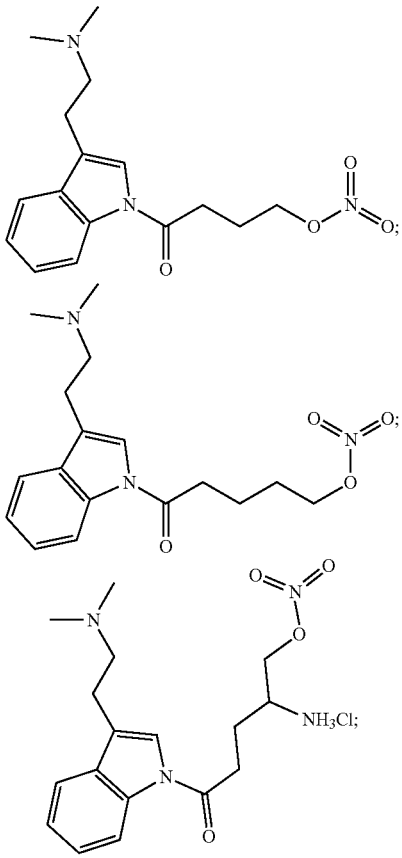

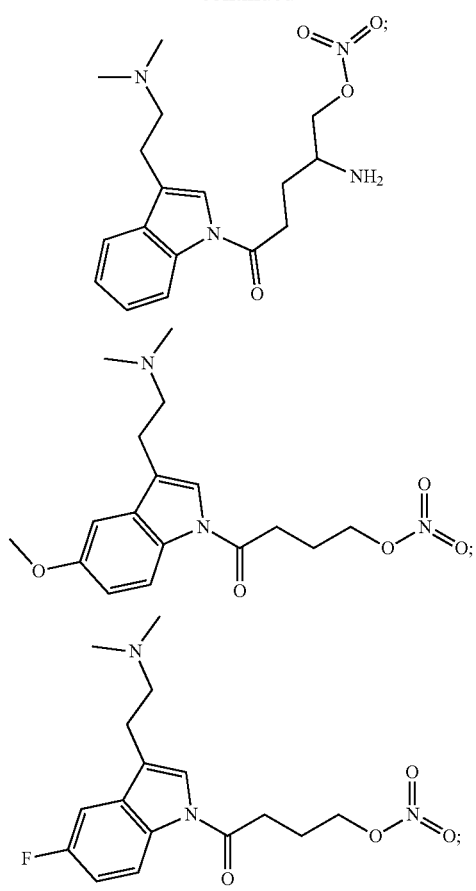
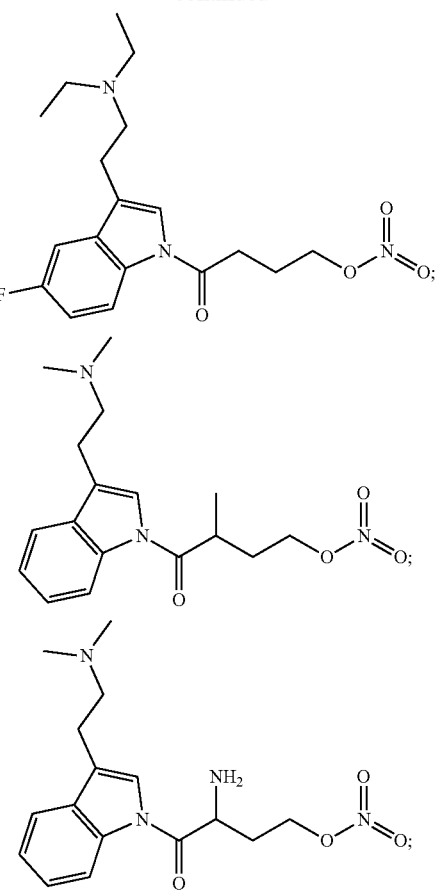
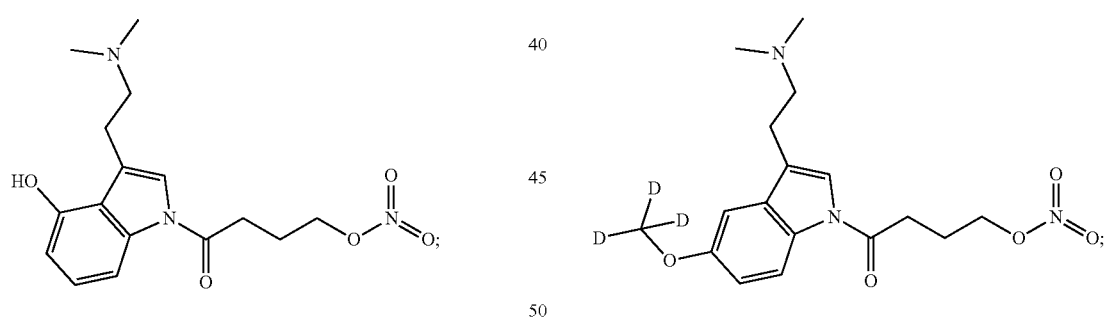
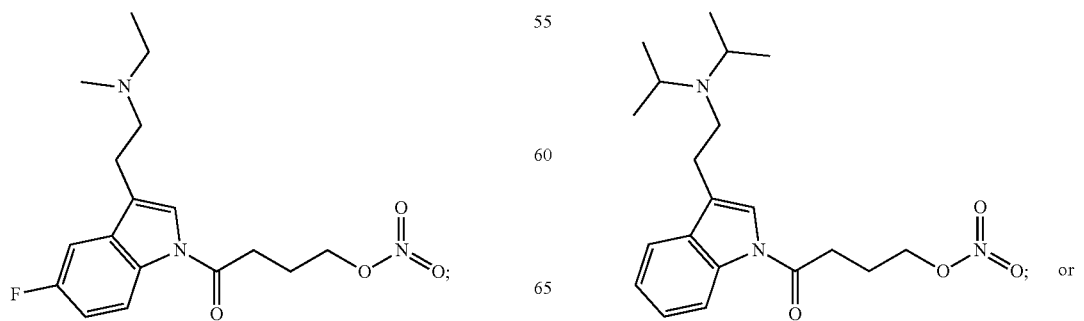

-continued

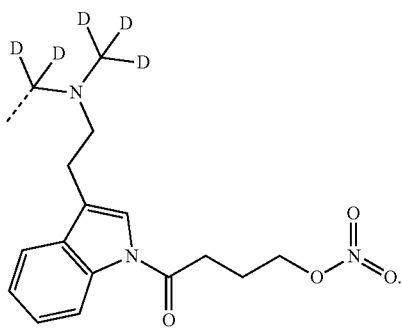

27. The compound of embodiment 26, having the following chemical formula:

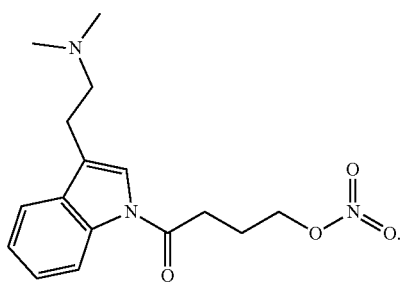 [SMILES: CN(C)CCc1cn(C(=O)CCCO[N+](=O)[O-])c2ccccc12]

28. The compound of embodiment 26, having the following chemical formula:

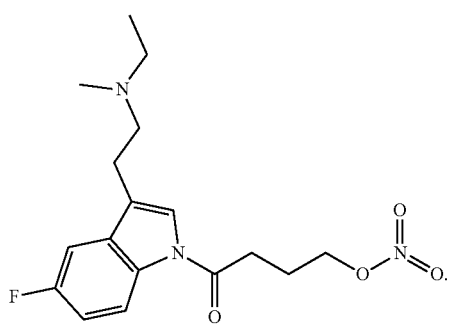 [SMILES: CCN(C)CCc1cn(C(=O)CCCO[N+](=O)[O-])c2ccc(F)cc12]

29. A pharmaceutical composition, comprising a compound of any one of embodiments 1-28 and a pharmaceutically acceptable excipient.

30. A method of treating a mental health disease or disorder, the method comprising administering a therapeutically effective amount of a compound of any one of embodiments 1-28 or pharmaceutical composition of embodiment 29.

31. A compound of Formula (I):

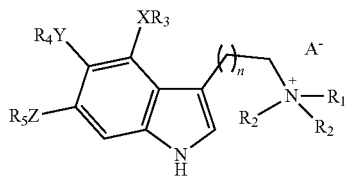

or a pharmaceutically acceptable salt thereof; wherein,
$R_1$, $R_3$, $R_4$ and $R_5$ are independently H, halogen, $C_1$-$C_6$ alkyl, —(C=O)(CR$_7$R$_7$')$_n$—ONO$_2$, or —(C=O)(CR$_7$R$_7$')$_m$—CH(NH$_2$)CH$_2$ONO$_2$;
$R_2$ is $C_1$-$C_6$ alkyl;
X, Y, and Z are independently absent, H, O, S, NH and —O—(P=O)OHO—;
m is 2, 3, or 4;
each n is independently 1, 2, 3, 4 or 5; and
$A^-$ is a pharmaceutically acceptable anion,
wherein at least one of $R_1$, $R_3$, $R_4$ and $R_5$ are —(C=O)(CR$_7$R$_7$')$_n$—ONO$_2$ or —(C=O)(CR$_7$R$_7$')$_m$—CH(NH$_2$)CH$_2$ONO$_2$.

32. The compound of embodiment 31, wherein $R_1$ is —(C=O)(CR$_7$R$_7$')$_n$—ONO$_2$.

33. The compound of embodiment 31, wherein $R_1$ is —(C=O)(CR$_7$R$_7$')$_m$—CH(NH$_2$)CH$_2$ONO$_2$.

34. The compound of embodiment 31, wherein $R_1$ is —(C=O)(CH$_2$)$_n$—ONO$_2$.

35. The compound of embodiment 31, wherein $R_1$ is —(C=O)(CH$_2$)$_m$—CH(NH$_2$)CH$_2$ONO$_2$.

36. The compound of embodiment 31, wherein $R_1$ is —(C=O)(CH$_2$)$_3$—ONO$_2$.

37. The compound of embodiment 31, wherein $R_1$ is —(C=O)(CH$_2$)$_2$—CH(NH$_2$)CH$_2$ONO$_2$.

38. The compound of any one of embodiments 31-37, wherein $R_2$ is a $C_1$-$C_3$ alkyl.

39. The compound of any one of embodiments 31-38, wherein $R_3$ is H and X is absent.

40. The compound of any one of embodiments 31-38, wherein $R_3$ is halogen and X is absent.

41. The compound of any one of embodiments 31-38, wherein $R_3$ is H and X is O.

42. The compound of any one of embodiments 31-38, wherein $R_3$ is $C_1$-$C_6$ alkyl and X is O.

43. The compound of any one of embodiments 31-42, wherein $R_4$ is H and Y is absent.

44. The compound of any one of embodiments 31-42, wherein $R_4$ is H and Y is O.

45. The compound of any one of embodiments 31-42, wherein $R_4$ is halogen and Y is absent.

46. The compound of any one of embodiments 31-42, wherein $R_4$ is $C_1$-$C_6$ alkyl and Y is O.

47. The compound of any one of embodiments 31-46, wherein $R_5$ is H and Z is absent.

48. The compound of any one of embodiments 31-46, wherein $R_5$ is H and Z is O.

49. The compound of any one of embodiments 31-46, wherein $R_5$ is halogen and Z is absent.

50. The compound of any one of embodiments 31-46, wherein $R_5$ is $C_1$-$C_6$ alkyl and Z is O.

51. A pharmaceutical composition, comprising a compound of any one of embodiments 31-50 and a pharmaceutically acceptable excipient.

52. A method of treating a mental health disease or disorder, the method comprising administering a therapeutically effective amount of a compound of any one of embodiments 31-50 or pharmaceutical composition of embodiment 51.

EXAMPLES

Example 1: Methods of Preparing the Compounds of the Present Disclosure

Synthesis of Compound 2-1

Prodrug 2-1 was synthesized from commercially available intermediate 2-1-1 and 2-1-3 in three steps and described in the Scheme 1.

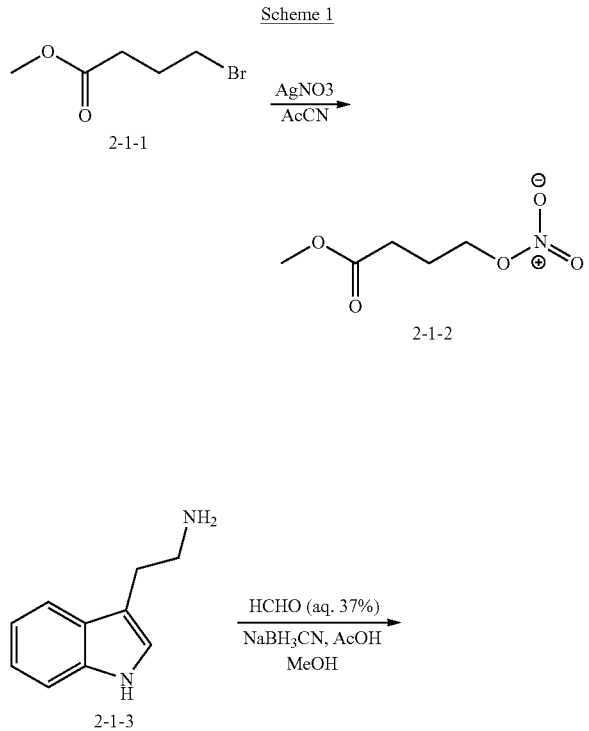

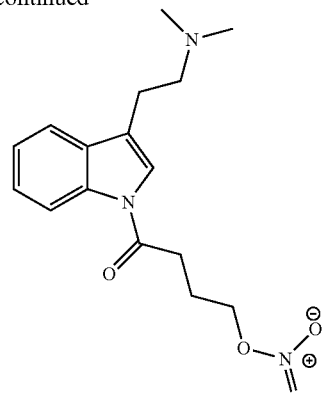

2-1

Synthesis of Intermediate 2-1-1

To a stirred solution of methyl 4-bromobutanoate, 2-1-1 (3 g, 16.5 mmol, 1.0 equiv) in acetonitrile was added $AgNO_3$ (7.0 g, 41.4 mmol, 2.5 equiv) in portions at room temperature under argon atmosphere. The resulting mixture was stirred for overnight at 80° C. under argon atmosphere. New pot could be detected by TLC. The resulting mixture was filtered, the filter cake was washed with acetonitrile (3×50 mL). The filtrate was concentrated under reduced pressure. The residue was dissolved in ethyl acetate (500 mL). The resulting mixture was washed with 2×500 mL of water. and then the resulting mixture was washed with 3×300 mL of brine. The combined organic layers dried over anhydrous $Na_2SO_4$. After filtration, the filtrate was concentrated under reduced pressure to afford methyl 4-(nitrooxy)butanoate, 2-1-2 (2.3 g, 85.08%) as a yellow oil. This crude product was used directly for the next step without further purification.

Synthesis of Intermediate 2-1-4 and final Product 1-(3-(2-(dimethylamino)ethyl)-1H-indol-1-yl)-4-(nitrooxy)butanoate (2-1)

To a stirred solution of tryptamine (200 mg, 1.2 mmol, 1.0 equiv) and $NaBH_3CN$ (235.3 mg, 3.7 mmol, 3.0 equiv), AcOH (0.2 mL) in MeOH was added formaldehyde solution (187.4 mg, 6.24 mmol, 5.0 equiv) dropwise at 0° C. under argon atmosphere. The resulting mixture was stirred for overnight at room temperature under argon atmosphere. Desired product could be detected by LCMS. The resulting mixture was filtered, the filter cake was washed with MeOH (3×10 mL). The filtrate was concentrated under reduced pressure. The residue was purified by silica gel column chromatography, eluted with PE/EA (1:1) to afford intermediate as a yellow solid. To a stirred solution of intermediate and methyl 4-(nitrooxy)butanoate (610.8 mg, 3.7 mmol, 3.0 equiv) in THF was added LiHMDS (313.3 mg, 1.8 mmol, 1.5 equiv) in THF dropwise at 0° C. under argon atmosphere. The resulting mixture was stirred for 1 h at 0° C. under argon atmosphere. Desired product could be detected by LCMS. The reaction was quenched with MeOH at 0° C. The resulting mixture was concentrated under vacuum. The residue was purified by reversed-phase flash chromatography with the following conditions: column, $C_{18}$ silica gel; mobile phase, MeCN in Water (0.1% FA), 5% to 80% gradient in 40 min; detector, UV 254 nm. to afford 25 mg of 1-(3-(2-(dimethylamino)ethyl)-1H-indol-1-yl)-4-(nitrooxy) butanoate (2-1) as a white solid. LCMS of 2-1: [M+H]⁺ 320.10

HNMR-2-1: (400 MHz, DMSO-d6) δ 8.07 (d, J=8.2 Hz, 1H), 7.62 (d, J=7.7 Hz, 1H), 7.52 (s, 1H), 7.36-7.25 (m, 2H), 4.79 (t, J=6.7 Hz, 2H), 4.47 (t, J=6.0 Hz, 2H), 2.80 (t, J=7.5 Hz, 2H), 2.57-2.40 (m, 4H), 2.22 (s, 6H).

What is claimed:

1. A compound of Formula (II):

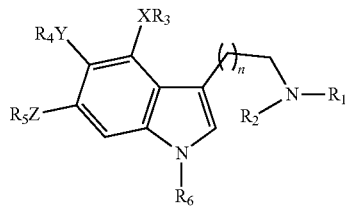

or a pharmaceutically acceptable salt thereof; wherein,
$R_3$, $R_4$, and $R_5$ are independently H, halogen, or $C_1$-$C_6$ alkyl;
$R_6$ is —(C=O)(CR$_7$R$_7$')$_n$—ONO$_2$, or —(C=O)(CR$_7$R$_7$')$_m$—CH(NH$_2$)CH$_2$ONO$_2$;
$R_1$ and $R_2$ are independently H or $C_1$-$C_6$ alkyl;
$R_7$ and $R_7$' are independently H, halogen, or $C_1$-$C_6$ alkyl;
X, Y, and Z are independently absent or O;
each m is 2, 3, or 4; and
each n is independently 1, 2, 3, 4 or 5.

2. The compound of claim 1, wherein $R_1$ is $C_1$-$C_6$ alkyl.
3. The compound of claim 1, wherein $R_1$ is methyl.
4. The compound of claim 1, wherein $R_1$ is H.
5. The compound of claim 1, wherein $R_2$ is $C_1$-$C_6$ alkyl.
6. The compound of claim 1, wherein $R_2$ is methyl.
7. The compound of claim 1, wherein $R_2$ is H.
8. The compound of claim 1, wherein $R_3$ is H and X is absent.
9. The compound of claim 1, wherein $R_3$ is halogen and X is absent.
10. The compound of claim 1, wherein $R_3$ is H and X is O.
11. The compound of claim 1, wherein $R_3$ is $C_1$-$C_6$ alkyl and X is O.
12. The compound of claim 1, wherein $R_4$ is H and Y is absent.
13. The compound of claim 1, wherein $R_4$ is H and Y is O.
14. The compound of claim 1, wherein $R_4$ is halogen and Y is absent.
15. The compound of claim 1, wherein $R_4$ is $C_1$-$C_6$ alkyl and Y is O.
16. The compound of claim 1, wherein $R_5$ is H and Z is absent.
17. The compound of claim 1, wherein $R_5$ is H and Z is O.
18. The compound of claim 1, wherein $R_5$ is halogen and Z is absent.
19. The compound of claim 1, wherein $R_5$ is $C_1$-$C_6$ alkyl and Z is absent.
20. The compound of claim 1, wherein $R_5$ is $C_1$-$C_6$ alkyl and Z is O.
21. The compound of claim 1, wherein $R_6$ is —(C=O)(CR$_7$R$_7$')$_n$—ONO$_2$.
22. The compound of claim 1, wherein $R_6$ is —(C=O)(CR$_7$R$_7$')$_m$—CH(NH$_2$)CH$_2$ONO$_2$.
23. The compound of claim 1, wherein $R_6$ is —(C=O)(CH$_2$)$_n$—ONO$_2$.
24. The compound of claim 1, wherein $R_6$ is —(C=O)(CH$_2$)$_m$—CH(NH$_2$)CH$_2$ONO$_2$.
25. The compound of claim 1, wherein $R_6$ is —(C=O)(CH$_2$)$_3$—ONO$_2$.
26. The compound of claim 1, having the following chemical formula:

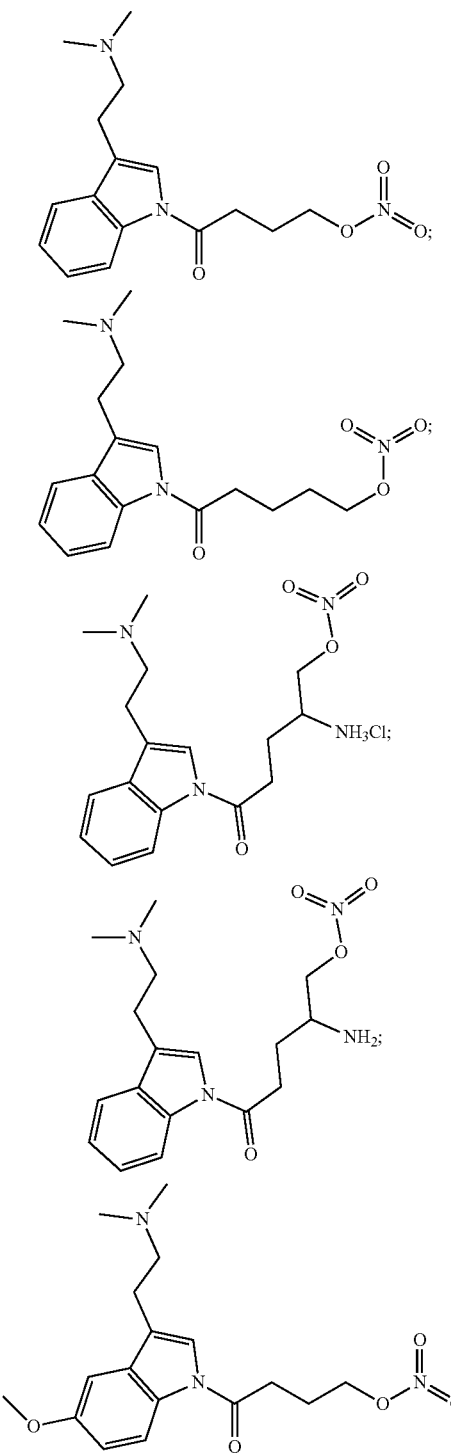

-continued
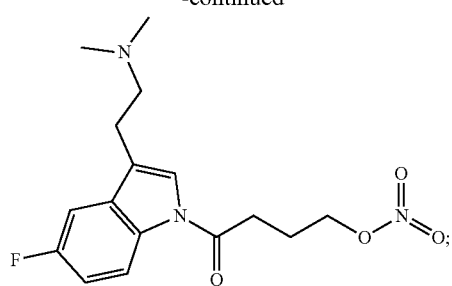
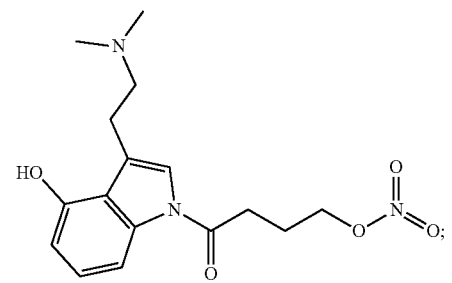
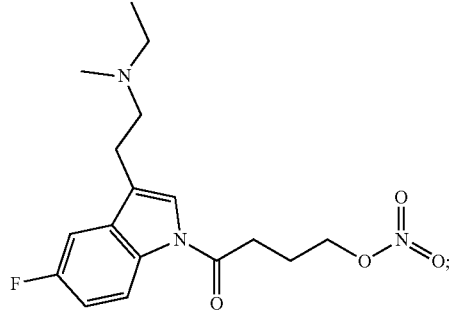 [SMILES: CCN(C)CCc1cn(C(=O)CCCO[N+](=O)[O-])c2ccc(F)cc12]
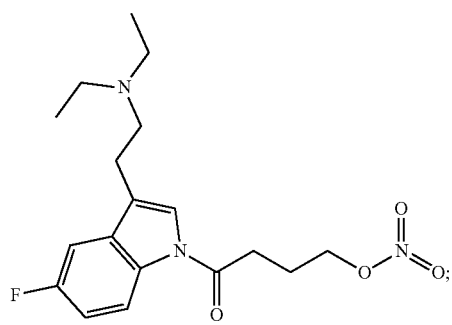
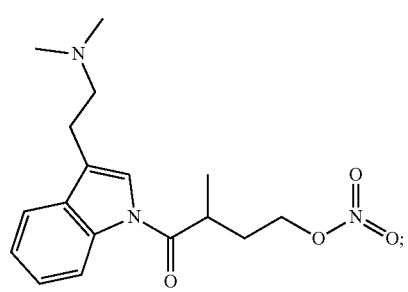
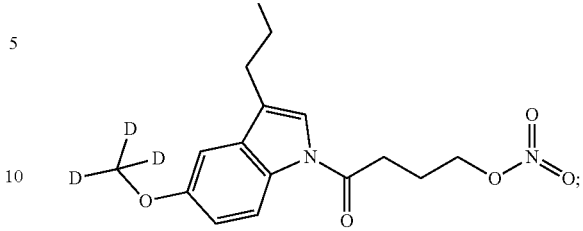
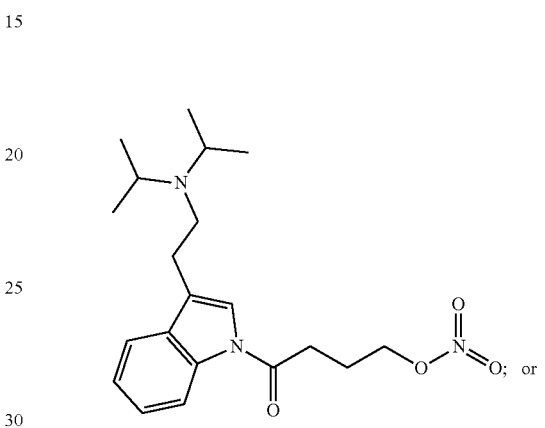
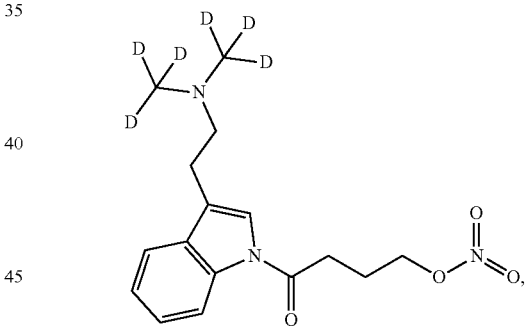
or a pharmaceutically acceptable salt thereof.
27. The compound of claim 26, having the following chemical formula:
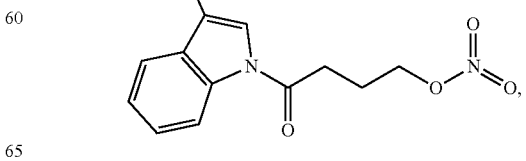
or a pharmaceutically acceptable salt thereof.

28. The compound of claim 26, having the following chemical formula:

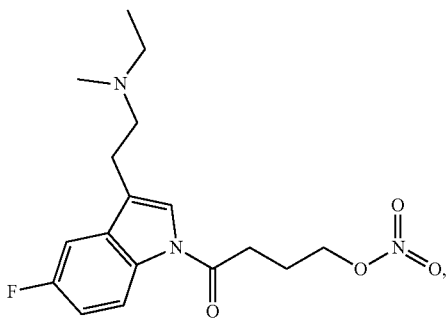

or a pharmaceutically acceptable salt thereof.

29. A pharmaceutical composition, comprising a compound of claim 1 and a pharmaceutically acceptable excipient.

30. A compound of chemical formula

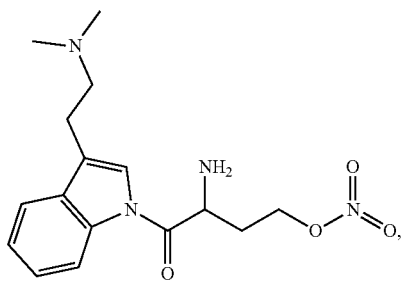 [SMILES: CN(C)CCc1cn(C(=O)C(N)CCO[N+](=O)[O-])c2ccccc12]

or a pharmaceutically acceptable salt thereof.

31. The compound of claim 26, having the following chemical formula:

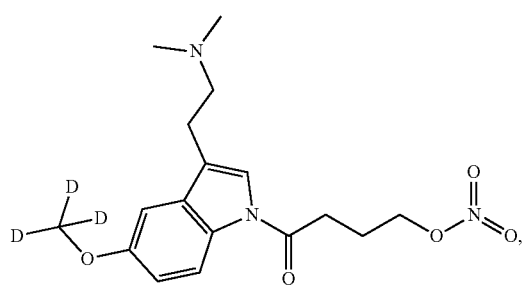 [SMILES: [2H]C([2H])([2H])Oc1ccc2c(c1)c(CCN(C)C)cn2C(=O)CCCO[N+](=O)[O-]]

or a pharmaceutically acceptable salt thereof.

32. The compound of claim 26, having the following chemical formula:

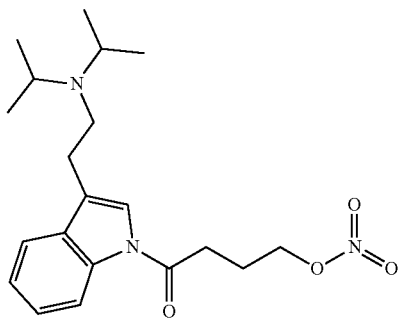 [SMILES: CC(C)N(CCc1cn(C(=O)CCCO[N+](=O)[O-])c2ccccc12)C(C)C]

or a pharmaceutically acceptable salt thereof.

33. The compound of claim 26, having the following chemical formula:

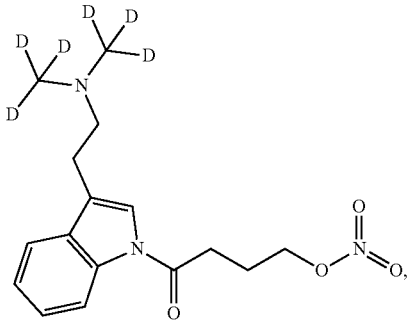 [SMILES: [2H]C([2H])([2H])N(CCc1cn(C(=O)CCCO[N+](=O)[O-])c2ccccc12)C([2H])([2H])[2H]]

or a pharmaceutically acceptable salt thereof.

* * * * *